US009567602B2

(12) United States Patent
Meade et al.

(10) Patent No.: US 9,567,602 B2
(45) **Date of Patent: *Feb. 14, 2017**

(54) COMBINED USE OF CRY1CA AND CRY1FA PROTEINS FOR INSECT RESISTANCE MANAGEMENT

(75) Inventors: Thomas Meade, Zionsville, IN (US); Kenneth Narva, Zionsville, IN (US); Nicholas P. Storer, Kensington, MD (US); Joel J. Sheets, Zionsville, IN (US); Aaron T. Woosley, Fishers, IN (US); Stephanie L. Burton, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 778 days.

This patent is subject to a terminal disclaimer.

(21) Appl. No.: 13/516,611

(22) PCT Filed: Dec. 16, 2010

(86) PCT No.: PCT/US2010/060817

§ 371 (c)(1),
(2), (4) Date: Aug. 30, 2012

(87) PCT Pub. No.: WO2011/075588

PCT Pub. Date: Jun. 23, 2011

(65) Prior Publication Data

US 2012/0317681 A1 Dec. 13, 2012

Related U.S. Application Data

(60) Provisional application No. 61/284,281, filed on Dec. 16, 2009.

(51) Int. Cl.
*C12N 15/82* (2006.01)
*A01N 63/02* (2006.01)

(52) U.S. Cl.
CPC ........... *C12N 15/8286* (2013.01); *A01N 63/02* (2013.01)

(58) Field of Classification Search
None
See application file for complete search history.

(56) References Cited

U.S. PATENT DOCUMENTS 4,695,455 A 9/1987 Barnes et al.
4,695,462 A 9/1987 Barnes et al.
5,135,867 A 8/1992 Payne et al.
5,169,760 A 12/1992 Wilcox
5,188,960 A 2/1993 Payne et al.
5,380,831 A 1/1995 Adang et al.
5,510,474 A 4/1996 Quail et al.
5,527,883 A 6/1996 Thompson et al.
5,593,881 A 1/1997 Thompson et al.
5,641,876 A 6/1997 McElroy
5,827,514 A 10/1998 Bradfisch et al.
5,866,784 A * 2/1999 Van Mellaert et al. ...... 800/302
5,932,209 A 8/1999 Thompson et al.
6,218,188 B1 * 4/2001 Cardineau ............ C07K 14/325 435/252.3
6,291,156 B1 * 9/2001 Estruch .................. A01N 63/00 435/4
6,551,962 B1 4/2003 Pershing et al.
6,673,990 B2 1/2004 Cardineau et al.
6,809,078 B2 * 10/2004 Baum .................. C07K 14/325 424/780
7,179,902 B2 2/2007 Cowen et al.
2003/0084606 A1 5/2003 Parker
2003/0101482 A1 * 5/2003 Baum et al. .................. 800/279
2004/0058860 A1 * 3/2004 Payne et al. .................... 514/12
2004/0133942 A1 7/2004 Miles
2004/0197916 A1 * 10/2004 Carozzi et al. ............... 435/468
2005/0155103 A1 7/2005 Baum
2005/0216969 A1 9/2005 Song
2006/0008877 A1 1/2006 Retallack et al.
2007/0006340 A1 1/2007 Lang
2008/0058262 A1 3/2008 Rasochova et al.
2008/0193974 A1 8/2008 Coleman et al.
2008/0311096 A1 12/2008 Lang et al.
2009/0093366 A1 4/2009 Wright et al.
2010/0235951 A1 9/2010 Van Rie et al.
2010/0269223 A1 10/2010 Lira et al.
2011/0047646 A1 * 2/2011 Manzanero ................... 800/279
2011/0099672 A1 * 4/2011 Gilbertson et al. ........ 800/300.1
2012/0331589 A1 12/2012 Meade et al.

FOREIGN PATENT DOCUMENTS

CN 103739683 A * 1/2014
EP 120516 10/1984

(Continued)

OTHER PUBLICATIONS van Frankenhuyzen. 2009. Insecticidal activity of Bacillus thuringiensis crystal proteins. Journal of Invertebrate Pathology 101: 1-16.*
Crickmore et al. 2014, "Bacillus thuringiensis toxin nomenclature" http://www.btnomenclature.info/.*
González-Cabrera et al Apr. 2006. Applied and Environmental Microbiology 72:2594-2600.*
Luo et al 1999, Appl. Environ. Microbiol. 65:457-464.*
Bates et al 2005, Nature Biotechnol. 23:57-62.*
Hernandez-Martinez et al 2009. Pest Manag. Sci 65: 645-650.*
Moar, W. J.: "Breathing new life into insect-resistant plants", Nature Biotechnology, Nature Publishing Group, New York, NY, vo. 21, No. 10, Oct. 1, 2003, pp. 1152-1154, XP002319567.
Bravo, A. et al: "How to cope with insect resistance to Bt toxins?", Trends in Biotechno(logy, Elsevier Publications, Cambridge, GB, vol. 26, No. 10. Oct. 1, 2008 (Oct. 1, 2008), pp. 573-579, XP025406825, ISSN: 0167-7799, DOI: 10.1016/J.Tibtech. 2008. 06.005 [retrieved on Aug. 14, 2008].

(Continued)

*Primary Examiner* — Anne Kubelik
*Assistant Examiner* — Karen Redden
(74) *Attorney, Agent, or Firm* — Ronald S. Maciak; Barnes & Thornburg LLP

(57) ABSTRACT

The subject invention includes methods and plants for controlling lepidopteran insects. The plants comprise a Cry1Fa insecticidal protein and a Cry1Ca insecticidal protein, in combination, to delay or prevent development of resistance by the insect(s).

17 Claims, 2 Drawing Sheets

(56) References Cited

FOREIGN PATENT DOCUMENTS

| | | | |
|---|---|---|---|
| EP | 400246 | | 12/1990 |
| WO | WO 93/16094 | | 8/1993 |
| WO | WO 97/13402 | | 4/1997 |
| WO | WO 01/14562 | | 3/2001 |
| WO | WO 2004/099447 | * | 11/2004 |
| WO | 2008/070845 | | 6/2008 |
| WO | WO 2008/080166 | A3 | 7/2008 |
| WO | WO 2008/145406 | A1 | 12/2008 |
| WO | WO 2009/132850 | * | 11/2009 |
| WO | WO 2009/132850 | A1 | 11/2009 |

OTHER PUBLICATIONS

Gutierrez, et al, "Physiologically based demographics of Bt cotton-pest interactions i.", Pink Bollworm Resistance< Refuge and Risk Ecological Modelling, vol. 191, 2006, pp. 346-359, XP005239868.

Avisar et al., "The Bacillus thuringiensis delta-endotoxin Cry1C as a potential bioinsecticide in plants," *Plant Science*, 176:315-324 (2009).

Hua et al., "Binding analyses of Bacillus thuringiensis Cry d-endotoxins using brush border membrane vesicles of Ostrinia nubilalis," *Applied and Environmental Microbiology*, 67(2): 872-879 (2001).

Marçon et al., "Baseline Susceptibility of the European Corn Borer (Lepidoptera: Crambidae) to *Bacillus thuringiensis* toxins," *J. Econ. Entomol.*, 92(2): 280-285 (1999).

McGaughey et al., "Bt resistance management," *Nature Biotechnology*, 16(2): 144-146 (1998).

Rang et al., "Competition of Bacillus thuringiensis Cry1 toxins for midgut binding sites: a basis for the development," *Curr. Microbiol.*, 49(1): 22-27 (2004).

Roush et al., "Two-toxin strategies for management of insecticidal transgenic crops: can pyramiding succeed where pesticide mixtures have not?," *Phil. Trans. R. Soc. Lond.*, 353: 1777-1786 (1998).

Stone, "A formula for determining degree of dominance in cases of monofactorial inheritance of resistance to chemicals," *Bull. W.H.O.*, 38(2): 325-329 (1968).

Tabashnik et al., "Delaying insect resistance to transgenic crops," *PNAS*, 105(49): 19029-19030 (Dec. 9, 2008).

* cited by examiner

SEQUENCE LISTING

```
<160> NUMBER OF SEQ ID NOS: 5

<210> SEQ ID NO 1
<211> LENGTH: 1164
<212> TYPE: PRT
<213> ORGANISM: Artificial Sequence
<220> FEATURE:
<223> OTHER INFORMATION: DIG-152 Chimeric protein

<400> SEQUENCE: 1

Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45

Asn Phe Val Pro Gly Gly Gly Phe Leu Val Gly Leu Ile Asp Phe Val
    50                  55                  60

Trp Gly Ile Val Gly Pro Ser Gln Trp Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
    130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255
```

-continued

```
Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
        275                 280                 285

Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
    370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445

Val Phe Ser Trp Thr His Arg Ser Ala Thr Leu Thr Asn Thr Ile Asp
    450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
        515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Phe Gly Ala Gly Ser Ile Ser Ser Gly Glu Leu Tyr Ile
        595                 600                 605

Asp Lys Ile Glu Ile Ile Leu Ala Asp Ala Thr Phe Glu Ala Glu Ser
    610                 615                 620

Asp Leu Glu Arg Ala Gln Lys Ala Val Asn Ala Leu Phe Thr Ser Ser
625                 630                 635                 640

Asn Gln Ile Gly Leu Lys Thr Asp Val Thr Asp Tyr His Ile Asp Arg
                645                 650                 655

Val Ser Asn Leu Val Glu Cys Leu Ser Asp Glu Phe Cys Leu Asp Glu
            660                 665                 670
```

```
Lys Lys Glu Leu Ser Glu Lys Val Lys His Ala Lys Arg Leu Ser Asp
        675                 680                 685

Glu Arg Asn Leu Leu Gln Asp Pro Asn Phe Arg Gly Ile Asn Arg Gln
    690                 695                 700

Leu Asp Arg Gly Trp Arg Gly Ser Thr Asp Ile Thr Ile Gln Gly Gly
705                 710                 715                 720

Asp Asp Val Phe Lys Glu Asn Tyr Val Thr Leu Leu Gly Thr Phe Asp
                725                 730                 735

Glu Cys Tyr Pro Thr Tyr Leu Tyr Gln Lys Ile Asp Glu Ser Lys Leu
            740                 745                 750

Lys Ala Tyr Thr Arg Tyr Gln Leu Arg Gly Tyr Ile Glu Asp Ser Gln
        755                 760                 765

Asp Leu Glu Ile Tyr Leu Ile Arg Tyr Asn Ala Lys His Glu Thr Val
    770                 775                 780

Asn Val Pro Gly Thr Gly Ser Leu Trp Pro Leu Ser Ala Pro Ser Pro
785                 790                 795                 800

Ile Gly Lys Cys Ala His His Ser His His Phe Ser Leu Asp Ile Asp
                805                 810                 815

Val Gly Cys Thr Asp Leu Asn Glu Asp Leu Gly Val Trp Val Ile Phe
            820                 825                 830

Lys Ile Lys Thr Gln Asp Gly His Ala Arg Leu Gly Asn Leu Glu Phe
        835                 840                 845

Leu Glu Glu Lys Pro Leu Val Gly Glu Ala Leu Ala Arg Val Lys Arg
    850                 855                 860

Ala Glu Lys Lys Trp Arg Asp Lys Arg Glu Lys Leu Glu Trp Glu Thr
865                 870                 875                 880

Asn Ile Val Tyr Lys Glu Ala Lys Glu Ser Val Asp Ala Leu Phe Val
                885                 890                 895

Asn Ser Gln Tyr Asp Arg Leu Gln Ala Asp Thr Asn Ile Ala Met Ile
            900                 905                 910

His Ala Ala Asp Lys Arg Val His Ser Ile Arg Glu Ala Tyr Leu Pro
        915                 920                 925

Glu Leu Ser Val Ile Pro Gly Val Asn Ala Ala Ile Phe Glu Glu Leu
    930                 935                 940

Glu Gly Arg Ile Phe Thr Ala Phe Ser Leu Tyr Asp Ala Arg Asn Val
945                 950                 955                 960

Ile Lys Asn Gly Asp Phe Asn Asn Gly Leu Ser Cys Trp Asn Val Lys
                965                 970                 975

Gly His Val Asp Val Glu Glu Gln Asn Asn His Arg Ser Val Leu Val
            980                 985                 990

Val Pro Glu Trp Glu Ala Glu Val  Ser Gln Glu Val Arg  Val Cys Pro
        995                 1000                1005

Gly Arg  Gly Tyr Ile Leu Arg  Val Thr Ala Tyr Lys  Glu Gly Tyr
    1010                1015                1020

Gly Glu  Gly Cys Val Thr Ile  His Glu Ile Glu Asn  Asn Thr Asp
    1025                1030                1035

Glu Leu  Lys Phe Ser Asn Cys  Val Glu Glu Glu Val  Tyr Pro Asn
    1040                1045                1050

Asn Thr  Val Thr Cys Asn Asp  Tyr Thr Ala Thr Gln  Glu Glu Tyr
    1055                1060                1065

Glu Gly  Thr Tyr Thr Ser Arg  Asn Arg Gly Tyr Asp  Gly Ala Tyr
    1070                1075                1080

Glu Ser  Asn Ser Ser Val Pro  Ala Asp Tyr Ala Ser  Ala Tyr Glu
```

-continued

```
    1085                1090                1095

Glu Lys  Ala Tyr Thr Asp Gly  Arg Arg Asp Asn Pro  Cys Glu Ser
    1100                1105                1110

Asn Arg  Gly Tyr Gly Asp Tyr  Thr Pro Leu Pro Ala  Gly Tyr Val
    1115                1120                1125

Thr Lys  Glu Leu Glu Tyr Phe  Pro Glu Thr Asp Lys  Val Trp Ile
    1130                1135                1140

Glu Ile  Gly Glu Thr Glu Gly  Thr Phe Ile Val Asp  Ser Val Glu
    1145                1150                1155

Leu Leu  Leu Met Glu Glu
    1160


<210> SEQ ID NO 2
<211> LENGTH: 1164
<212> TYPE: PRT
<213> ORGANISM: Artificial Sequence
<220> FEATURE:
<223> OTHER INFORMATION: DIG-109 chimeric protein

<400> SEQUENCE: 2

Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45

Asn Phe Val Pro Gly Gly Gly Phe Leu Val Gly Leu Ile Asp Phe Val
    50                  55                  60

Trp Gly Ile Val Gly Pro Ser Gln Trp Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
    130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
```

-continued

```
        275                 280                 285

Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
    370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445

Val Phe Ser Trp Thr His Arg Ser Ala Thr Leu Thr Asn Thr Ile Asp
    450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
        515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Phe Gly Ala Gly Ser Ile Ser Ser Gly Glu Leu Tyr Ile
        595                 600                 605

Asp Lys Ile Glu Ile Ile Leu Ala Asp Ala Thr Leu Glu Ala Glu Ser
    610                 615                 620

Asp Leu Glu Arg Ala Gln Lys Ala Val Asn Ala Leu Phe Thr Ser Ser
625                 630                 635                 640

Asn Gln Ile Gly Leu Lys Thr Asp Val Thr Asp Tyr His Ile Asp Arg
                645                 650                 655

Val Ser Asn Leu Val Glu Cys Leu Ser Asp Glu Phe Cys Leu Asp Glu
            660                 665                 670

Lys Lys Glu Leu Ser Glu Lys Val Lys His Ala Lys Arg Leu Ser Asp
        675                 680                 685

Glu Arg Asn Leu Leu Gln Asp Pro Asn Phe Arg Gly Ile Asn Arg Gln
    690                 695                 700
```

-continued

Leu Asp Arg Gly Trp Arg Gly Ser Thr Asp Ile Thr Ile Gln Gly Gly
705 710 715 720

Asp Asp Val Phe Lys Glu Asn Tyr Val Thr Leu Leu Gly Thr Phe Asp
725 730 735

Glu Cys Tyr Pro Thr Tyr Leu Tyr Gln Lys Ile Asp Glu Ser Lys Leu
740 745 750

Lys Ala Tyr Thr Arg Tyr Gln Leu Arg Gly Tyr Ile Glu Asp Ser Gln
755 760 765

Asp Leu Glu Ile Tyr Leu Ile Arg Tyr Asn Ala Lys His Glu Thr Val
770 775 780

Asn Val Pro Gly Thr Gly Ser Leu Trp Pro Leu Ser Ala Pro Ser Pro
785 790 795 800

Ile Gly Lys Cys Ala His His Ser His His Phe Ser Leu Asp Ile Asp
805 810 815

Val Gly Cys Thr Asp Leu Asn Glu Asp Leu Gly Val Trp Val Ile Phe
820 825 830

Lys Ile Lys Thr Gln Asp Gly His Ala Arg Leu Gly Asn Leu Glu Phe
835 840 845

Leu Glu Glu Lys Pro Leu Val Gly Glu Ala Leu Ala Arg Val Lys Arg
850 855 860

Ala Glu Lys Lys Trp Arg Asp Lys Arg Glu Lys Leu Glu Trp Glu Thr
865 870 875 880

Asn Ile Val Tyr Lys Glu Ala Lys Glu Ser Val Asp Ala Leu Phe Val
885 890 895

Asn Ser Gln Tyr Asp Arg Leu Gln Ala Asp Thr Asn Ile Ala Met Ile
900 905 910

His Ala Ala Asp Lys Arg Val His Ser Ile Arg Glu Ala Tyr Leu Pro
915 920 925

Glu Leu Ser Val Ile Pro Gly Val Asn Ala Ala Ile Phe Glu Glu Leu
930 935 940

Glu Gly Arg Ile Phe Thr Ala Phe Ser Leu Tyr Asp Ala Arg Asn Val
945 950 955 960

Ile Lys Asn Gly Asp Phe Asn Asn Gly Leu Ser Cys Trp Asn Val Lys
965 970 975

Gly His Val Asp Val Glu Glu Gln Asn Asn His Arg Ser Val Leu Val
980 985 990

Val Pro Glu Trp Glu Ala Glu Val Ser Gln Glu Val Arg Val Cys Pro
995 1000 1005

Gly Arg Gly Tyr Ile Leu Arg Val Thr Ala Tyr Lys Glu Gly Tyr
1010 1015 1020

Gly Glu Gly Cys Val Thr Ile His Glu Ile Glu Asn Asn Thr Asp
1025 1030 1035

Glu Leu Lys Phe Ser Asn Cys Val Glu Glu Glu Val Tyr Pro Asn
1040 1045 1050

Asn Thr Val Thr Cys Asn Asp Tyr Thr Ala Thr Gln Glu Glu Tyr
1055 1060 1065

Glu Gly Thr Tyr Thr Ser Arg Asn Arg Gly Tyr Asp Gly Ala Tyr
1070 1075 1080

Glu Ser Asn Ser Ser Val Pro Ala Asp Tyr Ala Ser Ala Tyr Glu
1085 1090 1095

Glu Lys Ala Tyr Thr Asp Gly Arg Arg Asp Asn Pro Cys Glu Ser
1100 1105 1110

-continued

```
Asn Arg  Gly Tyr Gly Asp Tyr  Thr Pro Leu Pro Ala  Gly Tyr Val
    1115                1120                1125

Thr Lys  Glu Leu Glu Tyr Phe  Pro Glu Thr Asp Lys  Val Trp Ile
    1130                1135                1140

Glu Ile  Gly Glu Thr Glu Gly  Thr Phe Ile Val Asp  Ser Val Glu
    1145                1150                1155

Leu Leu  Leu Met Glu Glu
    1160


<210> SEQ ID NO 3
<211> LENGTH: 3492
<212> TYPE: DNA
<213> ORGANISM: Artificial Sequence
<220> FEATURE:
<223> OTHER INFORMATION: DIG-109 maize-optimized coding region

<400> SEQUENCE: 3

atggataaca accccaacat taacgagtgc atcccgtaca actgcctctc gaatccagaa     60

gaagtgctct tggatggcga gaggatttcg actggcaaca gctccatcga catttccctc    120

tccttggttc agttccttgt gtctaacttc gtccctggcg gtggcttcct tgttggcctt    180

atcgacttcg tctggggaat tgtcggaccc tcccagtggg atgcgtttct ggtgcagata    240

gagcagctga tcaacgagag gatcgctgag ttcgcgagaa atgctgcaat cgccaacctt    300

gaagggcttg gcaacaactt caacatctac gtggaggcgt tcaaggagtg ggaagaggac    360

cctaagaatc cagcgaccag aacgagggtt atagatcggt tccgcatcct cgatggcctt    420

ttggagaggg acatcccgag cttccgcatt tcgggatttg aggttcctct gctctcagtc    480

tacgctcaag ctgctaatct gcatctggcc atcttgaggg attcagtcat ctttggcgaa    540

cgctggggtc ttacgactat caacgtgaac gagaactaca atcggttgat tcggcacata    600

gacgagtatg ccgaccactg tgctaacacc tacaataggg gtctgaacaa tctgccaaag    660

tcaacgtatc aagactggat aacctacaat aggctcagac gggacctcac tctcaccgtg    720

ctggacatag ctgccttctt tccgaactac gacaaccgga gatatcctat tcaacccgtt    780

ggtcagctca ctcgcgaggt ctacaccgat cccctcatca acttcaatcc ccagctgcaa    840

tcggtcgcac agctgcccac cttcaatgtg atggaaaact cagcgatccg gaatccccat    900

ctgtttgaca tacttaacaa cctcactatc ttcaccgatt ggttttcagt tggacgcaac    960

ttctactggg gagggcacag agtgatttca agcctcattg gaggagggaa cattacatcg   1020

cctatctatg gaagggaggc caaccaagag ccaccaaggt ctttcacctt caacggtccg   1080

gtgttcagaa cacttagcaa tcccacattg cgcttgctgc aacagccgtg gccagcacca   1140

ccattcaatc tgaggggagt ggagggtgtg gagttctcga cgcctacaaa ctcctttacg   1200

tacagaggca gagggacagt ggactcactg acagaactcc cacctgagga caactctgtt   1260

cctccgaggg agggctactc gcaccggctt tgccatgcca ccttcgtcca gaggtctggc   1320

acgccttttc tgaccactgg ggttgtcttt agctggactc accgctcagc gacgctgacc   1380

aacacaatcg acccagagag gatcaatcag atccctctgg tgaagggctt tcgcgtttgg   1440

ggtggcacaa gcgtgatcac cggacctggt ttcactggtg gggatatcct cagacgcaat   1500

acgtttggcg atttcgtgag ccttcaagtc aacatcaatt ccccaatcac ccagagatat   1560

cggctccgct tcagatacgc ctcatccaga gacgcaaggg tcatcgtcct tactggagca   1620

gccagcaccg gagtcggagg ccaagttagc gtcaacatgc cgttgcagaa aacgatggaa   1680

atcggtgaaa acctcaccag cagaaccttt cgctatacag atttcagcaa ccctttctcc   1740
```

ttcagagcca atccggacat aatcggcata tccgagcagc ccttgttcgg tgctgggtcc 1800
atctcttctg gcgagctgta catcgacaag attgagatca ttctcgcaga tgcgactctc 1860
gaggctgaat cggatcttga aagggcacag aaggcagtca acgctctctt caccagctca 1920
aatcagattg gccttaagac cgatgttact gactatcata tcgacagagt ttctaacctt 1980
gtcgagtgcc tctccgacga gttctgtctc gacgaaaaga aggaactctc cgagaaagtg 2040
aagcacgcga aacgcctctc ggatgaacgg aacttgctgc aagatccgaa cttcagaggc 2100
atcaatcgcc agttggatag aggctggagg ggatcaaccg acataaccat tcaaggtggg 2160
gatgatgtgt tcaaggaaaa ctacgtgaca ttgctgggca ccttcgacga gtgctatccc 2220
acgtatctct atcagaagat tgacgagtcc aagctcaaag cctacacacg ctatcagctc 2280
agaggctaca ttgaggactc tcaagacctc gaaatctact tgatcagata caacgccaag 2340
cacgagacgg tgaacgtccc tgggactggg tcactgtggc cactgtcggc accctcgcca 2400
atcggaaagt gcgctcacca cagccaccac ttctcccttg acatagatgt tgggtgtacg 2460
gacttgaatg aggatctggg tgtgtgggtg atctttaaga tcaagaccca agatggtcat 2520
gcgaggcttg gcaaccttga gttccttgaa gagaagcctt tggtcggaga ggcactggct 2580
cgcgtgaaga gggctgagaa gaaatggagg gacaagaggg agaaactgga gtgggagacc 2640
aacatagtgt acaaggaggc caaggagtca gtggacgcac tgtttgtcaa ttcccagtat 2700
gataggctcc aagcggacac gaacatcgcc atgatccatg cagcggacaa gagggttcac 2760
tccataaggg aggcctatct tccggagctg tcagtgattc ctggggtcaa cgcagccatc 2820
tttgaggaat tggaagggag gatcttcacc gctttctctc tgtacgacgc tcggaacgtc 2880
atcaagaatg gtgatttcaa caatggactc agctgctgga acgtgaaagg gcatgtcgat 2940
gttgaagaac agaacaatca ccgcagcgtg ctggtggttc cggagtggga agccgaggtc 3000
tcacaagaag tcagagtgtg ccctgggagg ggttacatct tgcgggtcac agcctacaag 3060
gaaggttatg gcgaaggctg tgtcacgatc catgagatcg aaaacaacac agacgagctg 3120
aagttttcca actgtgttga ggaggaggtc tatcctaaca atactgttac gtgcaacgac 3180
tacacagcca ctcaagagga gtacgagggc acttacacct ctcgcaacag aggctacgac 3240
ggtgcctacg agtcaaacag ctccgtgcca gcggactacg cctcggctta cgaagagaag 3300
gcgtacaccg acggtcggag ggataacccg tgcgagagca atagaggcta tggcgactac 3360
actcctctcc cagctggcta cgtgaccaag gagttggagt actttccgga gacagacaaa 3420
gtctggattg agattggaga gacagaaggc acgttcatcg tggactctgt tgaactcttg 3480
ctgatggagg ag 3492

<210> SEQ ID NO 4
<211> LENGTH: 605
<212> TYPE: PRT
<213> ORGANISM: Artificial Sequence
<220> FEATURE:
<223> OTHER INFORMATION: Cry1Fa

<400> SEQUENCE: 4

Met Glu Asn Asn Ile Gln Asn Gln Cys Val Pro Tyr Asn Cys Leu Asn
1 5 10 15

Asn Pro Glu Val Glu Ile Leu Asn Glu Glu Arg Ser Thr Gly Arg Leu
20 25 30

Pro Leu Asp Ile Ser Leu Ser Leu Thr Arg Phe Leu Leu Ser Glu Phe
35 40 45

-continued

```
Val Pro Gly Val Gly Val Ala Phe Gly Leu Phe Asp Leu Ile Trp Gly
    50                  55                  60

Phe Ile Thr Pro Ser Asp Trp Ser Leu Phe Leu Leu Gln Ile Glu Gln
65                  70                  75                  80

Leu Ile Glu Gln Arg Ile Glu Thr Leu Glu Arg Asn Arg Ala Ile Thr
                85                  90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
        115                 120                 125

Arg Ile Arg Phe Ala Asn Thr Asp Asp Ala Leu Ile Thr Ala Ile Asn
    130                 135                 140

Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
                165                 170                 175

Gly Gln Gly Trp Gly Leu Asp Ile Ala Thr Val Asn Asn His Tyr Asn
            180                 185                 190

Arg Leu Ile Asn Leu Ile His Arg Tyr Thr Lys His Cys Leu Asp Thr
        195                 200                 205

Tyr Asn Gln Gly Leu Glu Asn Leu Arg Gly Thr Asn Thr Arg Gln Trp
    210                 215                 220

Ala Arg Phe Asn Gln Phe Arg Arg Asp Leu Thr Leu Thr Val Leu Asp
225                 230                 235                 240

Ile Val Ala Leu Phe Pro Asn Tyr Asp Val Arg Thr Tyr Pro Ile Gln
                245                 250                 255

Thr Ser Ser Gln Leu Thr Arg Glu Ile Tyr Thr Ser Ser Val Ile Glu
            260                 265                 270

Asp Ser Pro Val Ser Ala Asn Ile Pro Asn Gly Phe Asn Arg Ala Glu
        275                 280                 285

Phe Gly Val Arg Pro Pro His Leu Met Asp Phe Met Asn Ser Leu Phe
    290                 295                 300

Val Thr Ala Glu Thr Val Arg Ser Gln Thr Val Trp Gly Gly His Leu
305                 310                 315                 320

Val Ser Ser Arg Asn Thr Ala Gly Asn Arg Ile Asn Phe Pro Ser Tyr
                325                 330                 335

Gly Val Phe Asn Pro Gly Gly Ala Ile Trp Ile Ala Asp Glu Asp Pro
            340                 345                 350

Arg Pro Phe Tyr Arg Thr Leu Ser Asp Pro Val Phe Val Arg Gly Gly
        355                 360                 365

Phe Gly Asn Pro His Tyr Val Leu Gly Leu Arg Gly Val Ala Phe Gln
    370                 375                 380

Gln Thr Gly Thr Asn His Thr Arg Thr Phe Arg Asn Ser Gly Thr Ile
385                 390                 395                 400

Asp Ser Leu Asp Glu Ile Pro Pro Gln Asp Asn Ser Gly Ala Pro Trp
                405                 410                 415

Asn Asp Tyr Ser His Val Leu Asn His Val Thr Phe Val Arg Trp Pro
            420                 425                 430

Gly Glu Ile Ser Gly Ser Asp Ser Trp Arg Ala Pro Met Phe Ser Trp
        435                 440                 445

Thr His Arg Ser Ala Thr Pro Thr Asn Thr Ile Asp Pro Glu Arg Ile
    450                 455                 460
```

-continued

Thr Gln Ile Pro Leu Val Lys Ala His Thr Leu Gln Ser Gly Thr Thr
465 470 475 480

Val Val Arg Gly Pro Gly Phe Thr Gly Gly Asp Ile Leu Arg Arg Thr
485 490 495

Ser Gly Gly Pro Phe Ala Tyr Thr Ile Val Asn Ile Asn Gly Gln Leu
500 505 510

Pro Gln Arg Tyr Arg Ala Arg Ile Arg Tyr Ala Ser Thr Thr Asn Leu
515 520 525

Arg Ile Tyr Val Thr Val Ala Gly Glu Arg Ile Phe Ala Gly Gln Phe
530 535 540

Asn Lys Thr Met Asp Thr Gly Asp Pro Leu Thr Phe Gln Ser Phe Ser
545 550 555 560

Tyr Ala Thr Ile Asn Thr Ala Phe Thr Phe Pro Met Ser Gln Ser Ser
565 570 575

Phe Thr Val Gly Ala Asp Thr Phe Ser Ser Gly Asn Glu Val Tyr Ile
580 585 590

Asp Arg Phe Glu Leu Ile Pro Val Thr Ala Thr Leu Glu
595 600 605

<210> SEQ ID NO 5
<211> LENGTH: 619
<212> TYPE: PRT
<213> ORGANISM: Artificial Sequence
<220> FEATURE:
<223> OTHER INFORMATION: Cry1Ca

<400> SEQUENCE: 5

Met Asp Asn Asn Pro Asn Ile Asn Glu Cys Ile Pro Tyr Asn Cys Leu
1 5 10 15

Ser Asn Pro Glu Glu Val Leu Leu Asp Gly Glu Arg Ile Ser Thr Gly
20 25 30

Asn Ser Ser Ile Asp Ile Ser Leu Ser Leu Val Gln Phe Leu Val Ser
35 40 45

Asn Phe Val Pro Gly Gly Gly Phe Leu Val Gly Leu Ile Asp Phe Val
50 55 60

Trp Gly Ile Val Gly Pro Ser Gln Trp Asp Ala Phe Leu Val Gln Ile
65 70 75 80

Glu Gln Leu Ile Asn Glu Arg Ile Ala Glu Phe Ala Arg Asn Ala Ala
85 90 95

Ile Ala Asn Leu Glu Gly Leu Gly Asn Asn Phe Asn Ile Tyr Val Glu
100 105 110

Ala Phe Lys Glu Trp Glu Glu Asp Pro Lys Asn Pro Ala Thr Arg Thr
115 120 125

Arg Val Ile Asp Arg Phe Arg Ile Leu Asp Gly Leu Leu Glu Arg Asp
130 135 140

Ile Pro Ser Phe Arg Ile Ser Gly Phe Glu Val Pro Leu Leu Ser Val
145 150 155 160

Tyr Ala Gln Ala Ala Asn Leu His Leu Ala Ile Leu Arg Asp Ser Val
165 170 175

Ile Phe Gly Glu Arg Trp Gly Leu Thr Thr Ile Asn Val Asn Glu Asn
180 185 190

Tyr Asn Arg Leu Ile Arg His Ile Asp Glu Tyr Ala Asp His Cys Ala
195 200 205

Asn Thr Tyr Asn Arg Gly Leu Asn Asn Leu Pro Lys Ser Thr Tyr Gln
210 215 220

-continued

```
Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
        275                 280                 285

Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
    370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445

Val Phe Ser Trp Thr His Arg Ser Ala Thr Leu Thr Asn Thr Ile Asp
    450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
        515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Phe Gly Ala Gly Ser Ile Ser Ser Gly Glu Leu Tyr Ile
        595                 600                 605

Asp Lys Ile Glu Ile Ile Leu Ala Asp Ala Thr
    610                 615
```

COMBINED USE OF CRY1CA AND CRY1FA PROTEINS FOR INSECT RESISTANCE MANAGEMENT

CROSS-REFERENCE TO RELATED APPLICATIONS

This is a national phase application, filed pursuant to 35 U.S.C. §371, of PCT application No. PCT/US10/60817 filed on Dec. 16, 2010, which claims the benefit of U.S. provisional application No. 61/284,281, filed on Dec. 16, 2009. The prior applications are incorporated herein by reference in their entirety.

BACKGROUND OF THE INVENTION

Humans grow corn for food and energy applications. Humans also grow many other crops, including soybeans and cotton. Insects eat and damage plants and thereby undermine these human efforts. Billions of dollars are spent each year to control insect pests and additional billions are lost to the damage they inflict. Synthetic organic chemical insecticides have been the primary tools used to control insect pests but biological insecticides, such as the insecticidal proteins derived from *Bacillus thuringiensis* (Bt), have played an important role in some areas. The ability to produce insect-resistant plants through transformation with Bt insecticidal protein genes has revolutionized modern agriculture and heightened the importance and value of insecticidal proteins and their genes.

Several Bt proteins have been used to create the insect-resistant transgenic plants that have been successfully registered and commercialized to date. These include Cry1Ab, Cry1Ac, Cry1F and Cry3Bb in corn, Cry1Ac and Cry2Ab in cotton, and Cry3A in potato.

The commercial products expressing these proteins express a single protein except in cases where the combined insecticidal spectrum of 2 proteins is desired (e.g., Cry1Ab and Cry3Bb in corn combined to provide resistance to lepidopteran pests and rootworm, respectively) or where the independent action of the proteins makes them useful as a tool for delaying the development of resistance in susceptible insect populations (e.g., Cry1Ac and Cry2Ab in cotton combined to provide resistance management for tobacco budworm).

That is, some of the qualities of insect-resistant transgenic plants that have led to rapid and widespread adoption of this technology also give rise to the concern that pest populations will develop resistance to the insecticidal proteins produced by these plants. Several strategies have been suggested for preserving the utility of Bt-based insect resistance traits which include deploying proteins at a high dose in combination with a refuge, and alternation with, or co-deployment of, different toxins (McGaughey et al. (1998), "B.t. Resistance Management," *Nature Biotechnol.* 16:144-146).

The proteins selected for use in an IRM stack need to exert their insecticidal effect independently so that resistance developed to one protein does not confer resistance to the second protein (i.e., there is not cross resistance to the proteins). If, for example, a pest population selected for resistance to "Protein A" is sensitive to "Protein B", one would conclude that there is not cross resistance and that a combination of Protein A and Protein B would be effective in delaying resistance to Protein A alone.

In the absence of resistant insect populations, assessments can be made based on other characteristics presumed to be related to mechanism of action and cross-resistance potential. The utility of receptor-mediated binding in identifying insecticidal proteins likely to not exhibit cross resistance has been suggested (van Mellaert et al. 1999). The key predictor of lack of cross resistance inherent in this approach is that the insecticidal proteins do not compete for receptors in a sensitive insect species.

In the event that two Bt toxins compete for the same receptor, then if that receptor mutates in that insect so that one of the toxins no longer binds to that receptor and thus is no longer insecticidal against the insect, it might be the case that the insect will also be resistant to the second toxin (which competitively bound to the same receptor). That is, the insect is said to be cross-resistant to both Bt toxins. However, if two toxins bind to two different receptors, this could be an indication that the insect would not be simultaneously resistant to those two toxins.

Cry1Fa is useful in controlling many lepidopteran pests species including the European corn borer (ECB; *Ostrinia nubilalis* (Hübner)) and the fall armyworm (FAW; *Spodoptera frugiperda*), and is active against the sugarcane borer (SCB; *Diatraea saccharalis*).

The Cry1Fa protein, as produced in corn plants containing event TC1507, is responsible for an industry-leading insect resistance trait for FA W control. Cry1Fa is further deployed in the HERCULEX®, SMARTSTAX™, and WIDESTRIKE™ products.

The ability to conduct (competitive or homologous) receptor binding studies using Cry1Fa protein is limited because the most common technique available for labeling proteins for detection in receptor binding assays inactivates the insecticidal activity of the Cry1Fa protein.

Additional Cry toxins are listed at the website of the official B.t. nomenclature committee (Crickmore et al.; lifesci.sussex.ac.uk/home/Neil_Crickmore/Bt/). See Appendix A, attached. There are currently nearly 60 main groups of "Cry" toxins (Cry1-Cry59), with additional Cyt toxins and VIP toxins and the like. Many of each numeric group have capital-letter subgroups, and the capital letter subgroups have lower-cased letter sub-subgroups. (Cry1 has A-L, and Cry1A has a-i, for example).

BRIEF SUMMARY OF THE INVENTION

The subject invention relates in part to the surprising discovery that a fall armyworm (*Spodoptera frugiperda*; FAW) population selected for resistance to the insecticidal activity of the Cry1Fa protein is not resistant to the insecticidal activity of the Cry1Ca protein. As one skilled in the art will recognize with the benefit of this disclosure, plants expressing these two insecticidal proteins, or insecticidal portions thereof, will be useful in delaying or preventing the development of resistance to either of these insecticidal proteins alone.

The subject invention is also supported by the discovery that Cry1Fa and Cry1Ca do not compete with each other for binding gut receptors from FAW (or from *Diatraea saccharalis* (sugarcane borer; SCB)).

The subject invention also relates in part to triple stacks or "pyramids" of three (or more) toxins, with Cry1Fa and Cry1C toxins being the base pair. One preferred pyramid provides at least two proteins providing non-cross-resistant activity against two pests—the FAW and the ECB (European corn borer; *Ostrinia nubilalis*): Cry1Fa plus Cry1Ca plus one or more anti-ECB toxins such as Cry1Ab. In some preferred pyramid embodiments, the selected toxins have three separate modes of action against FAW. Preferred pyramid combinations are Cry1Fa plus Cry1Ca plus another toxin/gene selected from the group consisting of Vip3Ab, Cry1D, Cry1Be, and Cry1E. Plants (and acreage planted with such plants) that produce these three toxins are included within the scope of the subject invention. Additional toxins/genes can also be added, but these particular triple stacks would, according to the subject invention, advantageously and surprisingly provide three modes of action against FAW. This can help to reduce or eliminate the requirement for refuge acreage. The subject invention also relates generally to the use of three insecticidal proteins (Cry proteins in some preferred embodiments) that do not compete with each other against a single target pest.

BRIEF DESCRIPTION OF THE SEQUENCE

Figure 1:
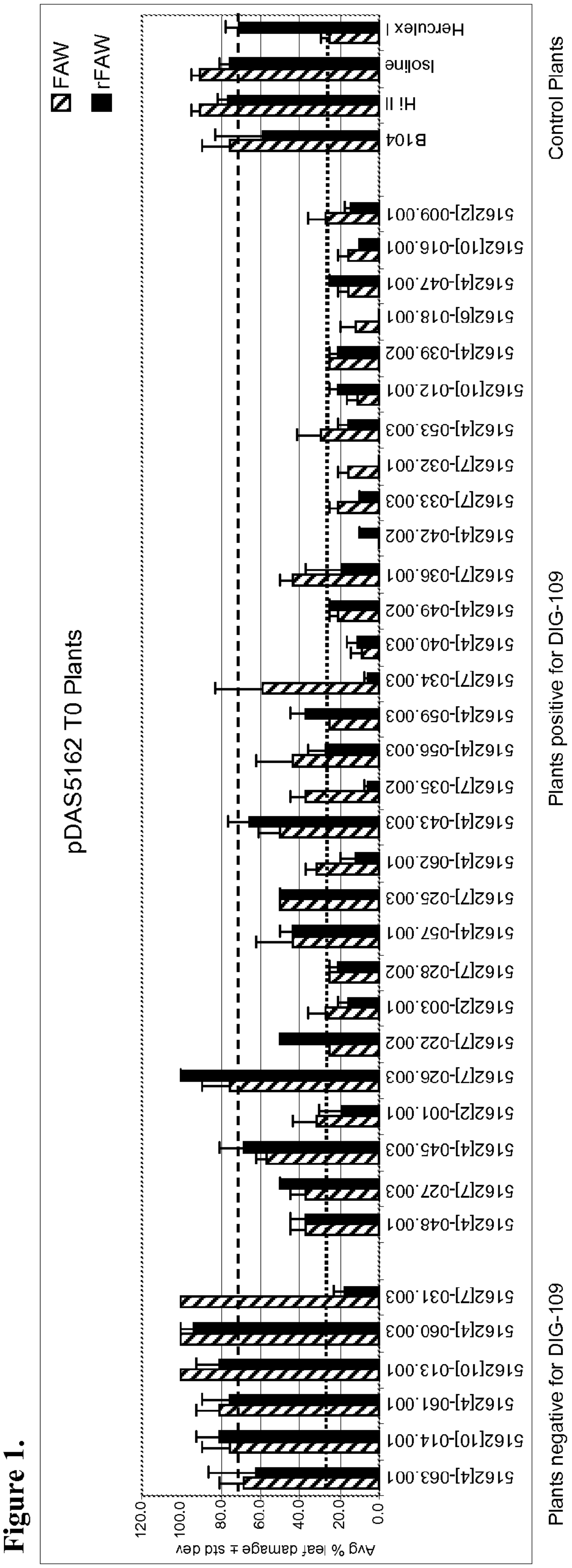
FIG. 1: Feeding damage ratings of maize leaf pieces challenged in vitro with neonate larvae of fall armyworm (FAW) and fall armyworm resistant to Cry1F (rFAW). Transgenic T0 plants selected after transformation with pDAS5162 were divided into two groups by immunoblot screening using antibody DIG152RPC1: plants which do not produce DIG-109 (on the left side of the Figure), and those which have detectable levels of DIG-109 (in the center of the Figure). DIG-109 Positive plants are ranked by expression level (left to right; lowest to highest). The HP analysis for DSM2 was completed on 36 pDAS5162-transformed lines. A simple integration event, defined as 1-2 copies of the gene, was detected in 95% of the samples. Bioassay results from Positive and Negative Control plants are shown on the right side of the Figure.

SEQ ID NO:1 Cry1Ca core/Cry1Ab protoxin chimeric protein 1164 aa (DIG-152) (pMYC2547 version)

SEQ ID NO:2 second Cry1Ca core/Cry1Ab protoxin chimeric protein 1164 aa (DIG-109) (maize version)

SEQ ID NO:3 maize-optimized CDS encoding DIG-109 3492 bp

SEQ ID NO:4 is a Cry1Fa core toxin.

SEQ ID NO:5 is a Cry1Ca core toxin.

DETAILED DESCRIPTION OF THE INVENTION

As reported herein, Cry1Ca toxin produced in transgenic corn and other plants (cotton and soybeans, for example) is very effective in controlling fall armyworm (FAW; *Spodoptera frugiperda*) that have developed resistance to Cry1Fa activity. Thus, the subject invention relates in part to the surprising discovery that fall armyworm resistant to Cry1Fa are susceptible (i.e., are not cross-resistant) to Cry1Ca.

The subject invention also relates in part to the surprising discovery that Cry1Ca toxin is effective at protecting plants (such as maize plants) from damage by Cry1Fa-resistant fall armyworm. For a discussion of this pest See e.g. Tabashnik, *PNAS* (2008), vol. 105 no. 49, 19029-19030.

The subject invention includes the use of Cry1Ca toxin to protect corn and other economically important plant species from damage and yield loss caused by fall armyworm feeding or to fall armyworm populations that have developed resistance to Cry1Fa.

The subject invention thus teaches an IRM stack to prevent or mitigate against the development of resistance by fall armyworm to Cry1Fa and/or Cry1Ca.

The present invention provides compositions for controlling lepidopteran pests comprising cells that produce a Cry1Fa core toxin-containing protein and a Cry1Ca core toxin-containing protein.

The invention further comprises a host transformed to produce both a Cry1Fa core toxin-containing protein and a Cry1Ca core toxin-containing protein, wherein said host is a microorganism or a plant cell. The subject polynucleotide(s) are preferably in a genetic construct under control (operably linked to/comprising) of a non-*Bacillus*-thuringiensis promoter. The subject polynucleotides can comprise codon usage for enhanced expression in a plant.

It is additionally intended that the invention provides a method of controlling lepidopteran pests comprising contacting said pests or the environment of said pests with an effective amount of a composition that contains a Cry1Fa core toxin-containing protein and further contains a Cry1Ca core toxin-containing protein.

An embodiment of the invention comprises a maize plant (and other plants—cotton and soybeans, for example) comprising a plant-expressible gene encoding a Cry1Ca core toxin-containing protein and a plant-expressible gene encoding a Cry1Fa core toxin-containing protein, and seed of such a plant.

A further embodiment of the invention comprises a maize plant (and other plants—cotton and soybeans, for example) wherein a plant-expressible gene encoding a Cry1Ca core toxin-containing protein and a plant-expressible gene encoding a Cry1Fa core toxin-containing protein have been introgressed into said maize plant, and seed of such a plant.

(For a review of Cry1C as a potential bioinsecticide in plants, see Avisar et al. 2009). Avisar D, Eilenberg H, Keller M, Reznik N, Segal M, Sneh B, Zilberstein A (2009) The *Bacillus thuringiensis* delta-endotoxin Cry1C as a potential bioinsecticide in plants. Plant Science 176:315-324.)

Insect Receptors.

As described in the Examples, competitive receptor binding studies using radiolabeled Cry1Ca core toxin protein show that the Cry1Fa core toxin protein does not compete for the high affinity binding site present in FAW insect tissues to which Cry1Ca binds. These results indicate that the combination of Cry1Fa and Cry1Ca proteins is an effective means to mitigate the development of resistance in FAW populations to Cry1Fa (and likewise, the development of resistance to Cry1Ca), and would likely increase the level of resistance to this pest in corn plants expressing both proteins.

Thus, based in part on the data described above and elsewhere herein, it is thought that co-production (stacking) of the Cry1Ca and Cry1Fa proteins can be used to produce a high dose IRM stack for FAW. Other proteins can be added to this combination to expand insect-control spectrum. For example in corn, the addition of Cry1Ab would create an IRM pyramid for control of European corn borer.

Another deployment option would be to use one or both of the Cry1Fa and Cry1Ca proteins in combination with the Cry1Ab protein to mitigate the development of resistance. Thus, another deployment option of the subject invention would be to use one or both of the Cry1Fa and Cry1Ca proteins in crop-growing regions where deployment of the Cry1Ab protein has become ineffective in controlling sugarcane borer due to the development of resistance populations. Accordingly, a preferred "triple stack" or "pyramid"

combination for use according to the subject invention is Cry1F plus Cry1C plus Cry1Ab.

The subject invention also relates in part to triple stacks or "pyramids" of three (or more) toxins, with Cry1Fa and Cry1C toxins being the base pair. One preferred pyramid provides at least two proteins providing non-cross-resistant activity against two pests—the FAW and the ECB (European corn borer; *Ostrinia nubilalis*): Cry1Fa plus Cry1Da plus one or more ECB toxins such as Cry1Ab (see US 2008 0311096), as Cry1F is active against both insects. Other ECB toxins include Cry1Be (see U.S. Ser. No. 61/284,290; filed Dec. 16, 2009), Cry1I (see U.S. Ser. No. 61/284,278; filed Dec. 16, 2009), Cry2Aa (see U.S. Ser. No. 61/284,278; filed Dec. 16, 2009) and DIG-3 (see US 2010 00269223). In some preferred pyramid embodiments, the selected toxins have three separate modes of action against FAW; these preferred pyramid combinations are Cry1Fa plus Cry1Ca plus another toxin/gene selected from the group consisting of Vip3Ab, Cry1D (see U.S. Ser. No. 61/284,252; filed Dec. 16, 2009), Cry1Be, and Cry1E (see U.S. Ser. No. 61/284, 278; filed Dec. 16, 2009). Plants (and acreage planted with such plants) that produce these three toxins are included within the scope of the subject invention. Additional toxins/genes can also be added, but these particular triple stacks would, according to the subject invention, advantageously and surprisingly provide three modes of action against FAW. This can help to reduce or eliminate the requirement for refuge acreage. A field thus planted of over 10 acres is thus included within the subject invention.

Other Vip3 toxins, for example, are listed in the attached Appendix A. Those GENBANK numbers can also be used to obtain the sequences for any of the genes and proteins disclosed or mentioned herein.

U.S. Pat. No. 5,188,960 and U.S. Pat. No. 5,827,514 describe Cry1Fa core toxin containing proteins suitable for use in carrying out the present invention. U.S. Pat. No. 6,218,188 describes plant-optimized DNA sequences encoding Cry1Fa core toxin-containing proteins that are suitable for use in the present invention.

Combinations of the toxins described in the subject invention can be used to control lepidopteran pests. Adult lepidopterans, for example, butterflies and moths, primarily feed on flower nectar and are a significant effector of pollination. Nearly all lepidopteran larvae, i.e., caterpillars, feed on plants, and many are serious pests. Caterpillars feed on or inside foliage or on the roots or stem of a plant, depriving the plant of nutrients and often destroying the plant's physical support structure. Additionally, caterpillars feed on fruit, fabrics, and stored grains and flours, ruining these products for sale or severely diminishing their value. As used herein, reference to lepidopteran pests refers to various life stages of the pest, including larval stages.

Some chimeric toxins of the subject invention comprise a full N-terminal core toxin portion of a Bt toxin and, at some point past the end of the core toxin portion, the protein has a transition to a heterologous protoxin sequence. The N-terminal, insecticidally active, toxin portion of a Bt toxin is referred to as the "core" toxin. The transition from the core toxin segment to the heterologous protoxin segment can occur at approximately the toxin/protoxin junction or, in the alternative, a portion of the native protoxin (extending past the core toxin portion) can be retained, with the transition to the heterologous protoxin portion occurring downstream.

As an example, one chimeric toxin of the subject invention, is a full core toxin portion of Cry1Fa (amino acids 1 to 601) and a heterologous protoxin (amino acids 602 to the C-terminus). In one preferred embodiment, the portion of a chimeric toxin comprising the protoxin is derived from a Cry1Ab protein toxin. As a second Example, a second chimeric toxin of the subject invention, as disclosed in SEQ ID NO:1 has the full core toxin portion of Cry1Ca (amino acids 1 to 619) and a heterologous protoxin (amino acids 620 to the C-terminus). In a preferred embodiment, the portion of a chimeric toxin comprising the protoxin is derived from a Cry1Ab protein toxin.

A person skilled in this art will appreciate that Bt toxins, even within a certain class such as Cry1F, will vary to some extent in length and the precise location of the transition from core toxin portion to protoxin portion. Typically, the Cry1Ca and Cry1Fa toxins are about 1150 to about 1200 amino acids in length. The transition from core toxin portion to protoxin portion will typically occur at between about 50% to about 60% of the full length toxin. The chimeric toxin of the subject invention will include the full expanse of this N-terminal core toxin portion. Thus, the chimeric toxin will comprise at least about 50% of the full length of the Cry1Fa Bt toxin protein or at least about 50% of the full length of the Cry1Ca Bt toxin protein. This will typically be at least about 590 amino acids. With regard to the protoxin portion, the full expanse of the Cry1Ab protoxin portion extends from the end of the core toxin portion to the C-terminus of the molecule.

Genes and Toxins.

The genes and toxins useful according to the subject invention include not only the full length sequences disclosed but also fragments of these sequences, variants, mutants, and fusion proteins which retain the characteristic pesticidal activity of the toxins specifically exemplified herein. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the claimed toxins.

As used herein, the boundaries represent approximately 95% (Cry1Fa's and 1Ca's), 78% (Cry1F's and Cry1C's), and 45% (Cry1's) sequence identity, per "Revision of the Nomenclature for the *Bacillus thuringiensis* Pesticidal Crystal Proteins," N. Crickmore, D. R. Zeigler, J. Feitelson, E. Schnepf, J. Van Rie, D. Lereclus, J. Baum, and D. H. Dean. Microbiology and Molecular Biology Reviews (1998) Vol 62: 807-813. These cut offs can also be applied to the core toxins only (for Cry1F and Cry1C toxins).

It should be apparent to a person skilled in this art that genes encoding active toxins can be identified and obtained through several means. The specific genes or gene portions exemplified herein may be obtained from the isolates deposited at a culture depository. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Genes that encode active fragments may also be obtained using a variety of restriction enzymes. Proteases may be used to directly obtain active fragments of these protein toxins.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments of genes encoding proteins that retain pesticidal activity are also included in this definition.

A further method for identifying the genes encoding the toxins and gene portions useful according to the subject invention is through the use of oligonucleotide probes. These probes are detectable nucleotide sequences. These sequences may be detectable by virtue of an appropriate label or may be made inherently fluorescent as described in International Application No. WO93/16094. As is well known in the art, if the probe molecule and nucleic acid sample hybridize by forming a strong bond between the two molecules, it can be reasonably assumed that the probe and sample have substantial homology. Preferably, hybridization is conducted under stringent conditions by techniques well-known in the art, as described, for example, in Keller, G. H., M. M. Manak (1987) DNA Probes, Stockton Press, New York, N.Y., pp. 169-170. Some examples of salt concentrations and temperature combinations are as follows (in order of increasing stringency): 2×SSPE or SSC at room temperature; 1×SSPE or SSC at 42° C.; 0.1×SSPE or SSC at 42° C.; 0.1×SSPE or SSC at 65° C. Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Variant Toxins.

Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid homology with an exemplified toxin. This amino acid homology will typically be greater than 75%, preferably be greater than 90%, and most preferably be greater than 95%. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 1 provides a listing of examples of amino acids belonging to each class.

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

Recombinant Hosts.

The genes encoding the toxins of the subject invention can be introduced into a wide variety of microbial or plant hosts. Expression of the toxin gene results, directly or indirectly, in the intracellular production and maintenance of the pesticide. Conjugal transfer and recombinant transfer can be used to create a Bt strain that expresses both toxins of the subject invention. Other host organisms may also be transformed with one or both of the toxin genes then used to accomplish the synergistic effect. With suitable microbial hosts, e.g., *Pseudomonas*, the microbes can be applied to the situs of the pest, where they will proliferate and be ingested. The result is control of the pest. Alternatively, the microbe hosting the toxin gene can be treated under conditions that prolong the activity of the toxin and stabilize the cell. The treated cell, which retains the toxic activity, then can be applied to the environment of the target pest.

Where the Bt toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera *Pseudomonas, Erwinia, Serratia, Klebsiella, Xanthomonas, Streptomyces, Rhizobium, Rhodopseudomonas, Methylophilius, Agrobactenum, Acetobacter, Lactobacillus, Arthrobacter, Azotobacter, Leuconostoc*, and *Alcaligenes*; fungi, particularly yeast, e.g., genera *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobactenium tumefaciens, Rhodopseudomonas spheroides, Xanthomonas campestris, Rhizobium melioti, Alcaligenes entrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

A wide variety of methods are available for introducing a Bt gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Treatment of Cells.

*Bacillus thuringiensis* or recombinant cells expressing the Bt toxins can be treated to prolong the toxin activity and stabilize the cell. The pesticide microcapsule that is formed comprises the Bt toxin or toxins within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the B.t. toxin gene or genes, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain at least a substantial portion of the bio-availability or bioactivity of the toxin.

Characteristics of particular interest in selecting a host cell for purposes of production include ease of introducing the B.t. gene or genes into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells. The cellular host containing the B.t. insecticidal gene or genes may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells producing the toxins of the invention can be cultured using standard art media and fermentation techniques. Upon completion of the fermentation cycle the bacteria can be harvested by first separating the B.t. spores and crystals from the fermentation broth by means well known in the art. The recovered B.t. spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulations.

Formulated bait granules containing an attractant and spores, crystals, and toxins of the B.t. isolates, or recombinant microbes comprising the genes obtainable from the B.t. isolates disclosed herein, can be applied to the soil. Formulated product can also be applied as a seed-coating or root treatment or total plant treatment at later stages of the crop cycle. Plant and soil treatments of B.t. cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest, e.g., foliage or soil, by spraying, dusting, sprinkling, or the like.

Plant Transformation.

A preferred recombinant host for production of the insecticidal proteins of the subject invention is a transformed plant. Genes encoding Bt toxin proteins, as disclosed herein, can be inserted into plant cells using a variety of techniques which are well known in the art. For example, a large number of cloning vectors comprising a replication system in *Escherichia coli* and a marker that permits selection of the transformed cells are available for preparation for the insertion of foreign genes into higher plants. The vectors comprise, for example, pBR322, pUC series, M13mp series, pACYC184, inter alia. Accordingly, the DNA fragment having the sequence encoding the Bt toxin protein can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and sufficiently described in EP 120 516, Lee and Gelvin (2008), Hoekema (1985), Fraley et al., (1986), and An et al., (1985), and is well established in the art.

Once the inserted DNA has been integrated in the plant genome, it is relatively stable. The transformation vector normally contains a selectable marker that confers on the transformed plant cells resistance to a biocide or an antibiotic, such as Bialaphos, Kanamycin, G418, Bleomycin, or Hygromycin, inter alia. The individually employed marker should accordingly permit the selection of transformed cells rather than cells that do not contain the inserted DNA.

A large number of techniques is available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If *Agrobacteria* are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in *Agrobacteria*. The intermediate vector can be transferred into *Agrobacterium tumefaciens* by means of a helper plasmid (conjugation). Binary vectors can replicate themselves both in *E. coli* and in *Agrobacteria*. They comprise a selection marker gene and a linker or polylinker which are framed by the Right and Left T-DNA border regions. They can be transformed directly into *Agrobacteria* (Holsters et al., 1978). The *Agrobacterium* used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831, which is hereby incorporated by reference. While some truncated toxins are exemplified herein, it is well-known in the Bt art that 130 kDa-type (full-length) toxins have an N-terminal half that is the core toxin, and a C-terminal half that is the protoxin "tail." Thus, appropriate "tails" can be used with truncated/core toxins of the subject invention. See e.g. U.S. Pat. No. 6,218,188 and U.S. Pat. No. 6,673,990. In addition, methods for creating synthetic Bt genes for use in plants are known in the art (Stewart and Burgin, 2007). One non-limiting example of a preferred transformed plant is a fertile maize plant comprising a plant expressible gene encoding a Cry1Fa protein, and further comprising a second plant expressible gene encoding a Cry1Ca protein.

Transfer (or introgression) of the Cry1Fa- and Cry1Ca-determined trait(s) into inbred maize lines can be achieved by recurrent selection breeding, for example by backcrossing. In this case, a desired recurrent parent is first crossed to a donor inbred (the non-recurrent parent) that carries the appropriate gene(s) for the Cry1F- and Cry1C-determined traits. The progeny of this cross is then mated back to the recurrent parent followed by selection in the resultant progeny for the desired trait(s) to be transferred from the non-recurrent parent. After three, preferably four, more preferably five or more generations of backcrosses with the recurrent parent with selection for the desired trait(s), the progeny will be heterozygous for loci controlling the trait(s) being transferred, but will be like the recurrent parent for most or almost all other genes (see, for example, Poehlman & Sleper (1995) Breeding Field Crops, 4th Ed., 172-175; Fehr (1987) Principles of Cultivar Development, Vol. 1: Theory and Technique, 360-376).

Insect Resistance Management (IRM) Strategies.

Roush et al., for example, outlines two-toxin strategies, also called "pyramiding" or "stacking," for management of insecticidal transgenic crops. (The Royal Society. *Phil. Trans. R. Soc. Lond. B.* (1998) 353, 1777-1786).

On their website, the United States Environmental Protection Agency (epa.gov/oppbppd1/biopesticides/pips/bt_corn_refuge_2006.htm) publishes the following requirements for providing non-transgenic (i.e., non-B.t.) refuges (a section or block of non-Bt crops/corn) for use with transgenic crops producing a single Bt protein active against target pests.

| "The specific structured requirements for corn borer-protected Bt (Cry1Ab or Cry1F) corn products are as follows: | |
|---|---|
| Structured refuges: | 20% non-Lepidopteran Bt corn refuge in Corn Belt;<br>50% non-Lepidopteran Bt refuge in Cotton Belt |

-continued

| "The specific structured requirements for corn borer-protected Bt (Cry1Ab or Cry1F) corn products are as follows: |
| --- |
| Blocks |
| Internal (i.e., within the Bt field) |
| External (i.e., separate fields within ½ mile (¼ mile if possible) of the Bt field to maximize random mating) |
| In-field Strips |
| Strips must be at least 4 rows wide (preferably 6 rows) to reduce the effects of larval movement" |

In addition, the National Corn Growers Association, on their website:

(ncga.com/insect-resistance-management-fact-sheet-bt-corn)

also provides similar guidance regarding the refuge requirements. For example:

| "Requirements of the Corn Borer IRM: |
| --- |
| Plant at least 20% of your corn acres to refuge hybrids |
| In cotton producing regions, refuge must be 50% |
| Must be planted within ½ mile of the refuge hybrids |
| Refuge can be planted as strips within the Bt field; the refuge strips must be at least 4 rows wide |
| Refuge may be treated with conventional pesticides only if economic thresholds are reached for target insect |
| Bt-based sprayable insecticides cannot be used on the refuge corn |
| Appropriate refuge must be planted on every farm with Bt corn" |

As stated by Roush et al. (on pages 1780 and 1784 right column, for example), stacking or pyramiding of two different proteins each effective against the target pests and with little or no cross-resistance can allow for use of a smaller refuge. Roush suggests that for a successful stack, a refuge size of less than 10% refuge, can provide comparable resistance management to about 50% refuge for a single (non-pyramided) trait. For currently available pyramided Bt corn products, the U.S. Environmental Protection Agency requires significantly less (generally 5%) structured refuge of non-Bt corn be planted than for single trait products (generally 20%).

There are various ways of providing the IRM effects of a refuge, including various geometric planting patterns in the fields (as mentioned above) and in-bag seed mixtures, as discussed further by Roush et al. (supra), and U.S. Pat. No. 6,551,962.

The above percentages, or similar refuge ratios, can be used for the subject double or triple stacks or pyramids. For triple stacks with three modes of action against a single target pest, a goal would be zero refuge (or less than 5% refuge, for example). This is particularly true for commercial acreage—of over 10 acres for example.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted. All temperatures are in degrees Celsius.

Unless specifically indicated or implied, the terms "a", "an", and "the" signify "at least one" as used herein.

EXAMPLE 1

Design of Chimeric Cry1Ca Core Toxins and Cry1Ab Protoxins

Chimeric Toxins. Chimeric proteins utilizing the core toxin domain of one Cry toxin fused to the protoxin segment of another Cry toxin have previously been reported, for example, in U.S. Pat. No. 5,593,881 and U.S. Pat. No. 5,932,209. A Cry1Ca3 delta endotoxin protein sequence is deposited as GenBank Accession Number AAA22343 under an obsolete terminology of CryIC(b).

Cry1Ca chimeric protein variants of this invention include chimeric toxins comprising an N-terminal core toxin segment derived from a Cry1Ca3 insecticidal toxin fused to a heterologous delta endotoxin protoxin segment at some point past the end of the core toxin segment. The transition from the core toxin to the heterologous protoxin segment can occur at approximately the native core toxin/protoxin junction or, in the alternative, a portion of the native protoxin (extending past the core toxin segment) can be retained, with the transition to the heterologous protoxin occurring downstream. In variant fashion, the core toxin and protoxin segments may comprise exactly the amino acid sequence of the native toxins from which they are derived, or may include amino acid additions, deletions, or substitutions that do not diminish, and may enhance, the biological function of the segments when fused to one another.

For example, a chimeric toxin of the subject invention comprises a core toxin segment derived from Cry1Ca3 and a heterologous protoxin. In a preferred embodiment of the invention, the core toxin segment derived from Cry1Ca3 (619 amino acids) is fused to a heterologous segment comprising a protoxin segment derived from a Cry1Ab delta-endotoxin (545 amino acids). The 1164 amino acid sequence of the chimeric protein, herein referred to as DIG-152, is disclosed as SEQ ID NO:1. A second preferred embodiment of the invention comprises a chimeric protein in which the Cry1Ca core toxin segment (619 amino acids) is joined to a second 545 amino acid protoxin segment derived from Cry1Ab The 1164 amino acid sequence of the second chimeric protein, referred to as DIG-109, is disclosed as SEQ ID NO:2 (maize optimized version). It is to be understood that other chimeric fusions comprising Cry1Ca core toxin variants and protoxins derived from Cry1Ab are within the scope of this invention.

It is noted that the DIG-152 and DIG-109 chimeric proteins are essentially functional equivalents of one another, differing in sequence only at a single position (amino acid 620, which joins the Cry1Ca core toxin segment to the Cry1Ab protoxin segment).

EXAMPLE 2

Construction of Expression Plasmids Encoding Chimeric Cry1Ca Core/Cry1Ab Protoxin Proteins and Expression in *Pseudomonas*

Standard cloning methods (as described in, for example, Sambrook et al., (1989) and Ausubel et al., (1995), and updates thereof) were used in the construction of *Pseudomonas fluorescens* (Pf) expression construct pMYC2547 engineered to produce a full-length DIG-152 chimeric protein (as disclosed in SEQ ID NO:1). Protein production was performed in *Pseudomonas fluorescens* strain MB214 (a derivative of strain MB101; *P. fluorescens* biovar I), having an insertion of a modified lac operon as disclosed in U.S.

Pat. No. 5,169,760. The basic cloning strategy entailed subcloning a DNA fragment encoding DIG-152 into plasmid vectors, whereby it is placed under the expression control of the Ptac promoter and the rrnBT1T2 terminator from plasmid pKK223-3 (PL Pharmacia, Milwaukee, Wis.). One such plasmid was named pMYC2547, and the MB214 isolate harboring this plasmid is named Dpf108.

Growth and Expression Analysis in Shake Flasks

Production of DIG-152 protein for characterization and insect bioassay was accomplished by shake-flask-grown *P. fluorescens* strain Dpf108. DIG-152 protein production driven by the Ptac promoter was conducted as described previously in U.S. Pat. No. 5,527,883. Details of the microbiological manipulations are available in Squires et al., (2004), US Patent Application 20060008877, US Patent Application 20080193974, and US Patent Application 20080058262, incorporated herein by reference. Expression was induced by addition of isopropyl-β-D-1-thiogalactopyranoside (IPTG) after an initial incubation of 24 hours at 30° with shaking. Cultures were sampled at the time of induction and at various times post-induction. Cell density was measured by optical density at 600 nm ($OD_{600}$).

Cell Fractionation and SDS-PAGE Analysis of Shake Flask Samples

At each sampling time, the cell density of samples was adjusted to $OD_{600}$=20 and 1 mL aliquots were centrifuged at 14000×g for five minutes. The cell pellets were frozen at −80°. Soluble and insoluble fractions from frozen shake flask cell pellet samples were generated using EasyLyse™ Bacterial Protein Extraction Solution (EPICENTRE® Biotechnologies, Madison, Wis.). Each cell pellet was resuspended in 1 mL EasyLyse™ solution and further diluted 1:4 in lysis buffer and incubated with shaking at room temperature for 30 minutes. The lysate was centrifuged at 14,000 rpm for 20 minutes at 4° and the supernatant was recovered as the soluble fraction. The pellet (insoluble fraction) was then resuspended in an equal volume of phosphate buffered saline (PBS; 11.9 mM $Na_2HPO_4$, 137 mM NaCl, 2.7 mM KCl, pH7.4).

Samples were mixed 1:1 with 2× Laemmli sample buffer containing β-mercaptoethanol (Sambrook et al., supra.) and boiled for 5 minutes prior to loading onto Criterion XT Bis-Tris 12% gels (Bio-Rad Inc., Hercules, Calif.). Electrophoresis was performed in the recommended XT MOPS buffer. Gels were stained with Bio-Safe Coomassie Stain according to the manufacturer's (Bio-Rad) protocol and imaged using the Alpha Innotech Imaging system (San Leandro, Calif.).

Inclusion Body Preparation.

DIG-152 protein inclusion body (IB) preparations were performed on cells from *P. fluorescens* fermentations that produced insoluble Bt insecticidal protein, as demonstrated by SDS-PAGE and MALDI-MS (Matrix Assisted Laser Desorption/Ionization Mass Spectrometry). *P. fluorescens* fermentation pellets were thawed in a 37° water bath. The cells were resuspended to 25% w/v in lysis buffer [50 mM Tris, pH 7.5, 200 mM NaCl, 20 mM EDTA disodium salt (Ethylenediaminetetraacetic acid), 1% Triton X-100, and 5 mM Dithiothreitol (DTT); 5 mL/L of bacterial protease inhibitor cocktail (Catalog #P8465; Sigma-Aldrich, St. Louis, Mo.) were added just prior to use]. The cells were suspended using a hand-held homogenizer at lowest setting (Tissue Tearor, BioSpec Products, Inc., Bartlesville, Okla.). Lysozyme (25 mg of Sigma L7651, from chicken egg white) was added to the cell suspension by mixing with a metal spatula, and the suspension was incubated at room temperature for one hour. The suspension was cooled on ice for 15 minutes, then sonicated using a Branson Sonifier 250 (two 1-minute sessions, at 50% duty cycle, 30% output). Cell lysis was checked by microscopy. An additional 25 mg of lysozyme were added if necessary, and the incubation and sonication were repeated. Following confirmation of cell lysis via microscopy, the lysate was centrifuged at 11,500×g for 25 minutes (4°) to form the IB pellet, and the supernatant was discarded. The IB pellet was resuspended with 100 mL lysis buffer, homogenized with the hand-held mixer and centrifuged as above. The IB pellet was repeatedly washed by resuspension (in 50 mL lysis buffer), homogenization, sonication, and centrifugation until the supernatant became colorless and the IB pellet became firm and off-white in color. For the final wash, the IB pellet was resuspended in sterile-filtered (0.22 μm) distilled water containing 2 mM EDTA, and centrifuged. The final pellet was resuspended in sterile-filtered distilled water containing 2 mM EDTA, and stored in 1 mL aliquots at −80°.

SDS-PAGE analysis and quantitation of protein in IB preparations was done by thawing a 1 mL aliquot of IB pellet and diluting 1:20 with sterile-filtered distilled water. The diluted sample was then boiled with 4× reducing sample buffer [250 mM Tris, pH6.8, 40% glycerol (v/v), 0.4% Bromophenol Blue (w/v), 8% SDS (w/v) and 8% β-mercaptoethanol (v/v)] and loaded onto a Novex® 4-20% Tris-Glycine, 12+2 well gel (Invitrogen) run with 1× Tris/Glycine/SDS buffer (BioRad). The gel was run for 60 min at 200 volts then stained with Coomassie Blue (50% G-250/50% R-250 in 45% methanol, 10% acetic acid), and destained with 7% acetic acid, 5% methanol in distilled water. Quantification of target bands was done by comparing densitometric values for the bands against Bovine Serum Albumin (BSA) standard samples run on the same gel to generate a standard curve.

Solubilization of Inclusion Bodies.

Six mL of DIG-152 inclusion body suspension from Pf clone DPf108 were centrifuged on the highest setting of an Eppendorf model 5415C microfuge (approximately 14,000×g) to pellet the inclusions. The storage buffer supernatant was removed and replaced with 25 mL of 100 mM sodium carbonate buffer, pH11, in a 50 mL conical tube. Inclusions were resuspended using a pipette and vortexed to mix thoroughly. The tube was placed on a gently rocking platform at 4° overnight to extract the target protein. The extract was centrifuged at 30,000×g for 30 min at 4°, and the resulting supernatant was concentrated 5-fold using an Amicon Ultra-15 regenerated cellulose centrifugal filter device (30,000 Molecular Weight Cutoff; Millipore). The sample buffer was then changed to 10 mM CAPS [3-(cyclohexamino)1-propanesulfonic acid] pH 10 using disposable PD-10 columns (GE Healthcare, Piscataway, N.J.).

Solubilization and Trypsin Activation of Inclusion Body Protein.

In some instances, DIG-152 inclusion body suspension from Pf clone DPf108 was centrifuged on the highest setting of an Eppendorf model 5415C microfuge (approximately 14,000×g) to pellet the inclusions. The storage buffer supernatant was removed and replaced with 100 mM CAPS, pH 11 to provide a protein concentration of approximately 50 mg/mL. The tube was rocked at room temperature for three hours to completely solubilize the protein. Trypsin was added at an amount equal to 5% to 10% (w:w, based on the initial weight of IB powder) and digestion was accomplished by incubation while rocking overnight at 4° or by rocking 90-120 minutes at room temperature. Insoluble material was removed by centrifugation at 10,000×g for 15 minutes, and the supernatant was applied to a MonoQ anion exchange column (10 mm by 10 cm). Activated DIG-152 protein was eluted (as determined by SDS-PAGE, see below) by a 0% to 100% 1 M NaCl gradient over 25 column volumes. Fractions containing the activated protein were pooled and, when necessary, concentrated to less than 10 mL using an Amicon Ultra-15 regenerated cellulose centrifugal filter device as above. The material was then passed through a Superdex 200 column (16 mm by 60 cm) in buffer containing 100 mM NaCl. 10% glycerol, 0.5% Tween-20 and 1 mM EDTA. It was determined by SDS-PAGE analysis that the activated (enzymatically truncated) protein elutes at 65 to 70 mL. Fractions containing the activated protein were pooled and concentrated using the centrifugal concentrator as above.

Gel Electrophoresis.

The concentrated protein preparations were prepared for electrophoresis by diluting 1:50 in NuPAGE® LDS sample buffer (Invitrogen) containing 5 mM DTT as a reducing agent and heated at 95° for 4 minutes. The sample was loaded in duplicate lanes of a 4-12% NuPAGE® gel alongside five BSA standards ranging from 0.2 μg to 2 μg/lane (for standard curve generation). Voltage was applied at 200 V using MOPS SDS running buffer (Invitrogen) until the tracking dye reached the bottom of the gel. The gel was stained with 0.2% Coomassie Blue G-250 in 45% methanol, 10% acetic acid, and destained, first briefly with 45% methanol, 10% acetic acid, and then at length with 7% acetic acid, 5% methanol until the background cleared. Following destaining, the gel was scanned with a BioRad Fluor-S MultiImager. The instrument's Quantity One Software v.4.5.2 was used to obtain background-subtracted volumes of the stained protein bands and to generate the BSA standard curve that was used to calculate the concentration of chimeric DIG-152 protein in the stock solution.

EXAMPLE 3

Insecticidal Activity of DIG-152 Protein Produced in *Pseudomonas fluorescens*

Insecticidal activity of the DIG-152 protein was demonstrated on larvae of the fall armyworm (FAW, *Spodoptera frugiperda* (J. E. Smith)) and on larvae of Cry1F-resistant FAW (rFAW).

Sample Preparation and Bioassays.

Inclusion body preparations (native full length protein or trypsin activated protein) were transferred to 10 mM CAPS pH10 buffer by exchange methods such as dialysis or PD-10 columns. The samples were then diluted appropriately in 10 mM CAPS pH 10, and all bioassays contained a control treatment consisting of this buffer, which served as a background check for mortality or growth inhibition.

Protein concentrations in bioassay buffer were estimated by gel electrophoresis using BSA to create a standard curve for gel densitometry, which was measured using a BioRad imaging system as above. Proteins in the gel matrix were stained with Coomassie Blue-based stain and destained before reading.

Purified proteins were tested for insecticidal activity in bioassays conducted with neonate Lepidopteran larvae on artificial insect diet. Larvae of FAW were hatched from eggs obtained from a colony maintained by a commercial insectary (Benzon Research Inc., Carlisle, Pa.). Larvae of rFAW were hatched from eggs harvested from a non-commercial colony (Dow AgroSciences, Indianapolis, Ind.).

The bioassays were conducted in 128-well plastic trays specifically designed for insect bioassays (C-D International, Pitman, N.J.). Each well contained 1.0 mL of multi-species Lepidoptera diet (Southland Products, Lake Village, Ark.). A 40 μL aliquot of protein sample was delivered by pipette onto the 1.5 $cm^2$ diet surface of each well (i.e. 26.7 $\mu L/cm^2$). Diet concentrations were calculated as the amount (ng) of DIG-152 protein per square centimeter of surface area in the well. The treated trays were held in a fume hood until the liquid on the diet surface had evaporated or was absorbed into the diet.

Within a few hours of eclosion, individual larvae were picked up with a moistened camel hair brush and deposited on the treated diet, one larva per well. The infested wells were then sealed with adhesive sheets of clear plastic, vented to allow gas exchange (C-D International). Bioassay trays were held under controlled environmental conditions [28°, approximately 40% Relative Humidity (RH), 16 hr:8 hr (light:dark)] for 5 days, after which time the total number of insects exposed to each protein sample, the number of dead insects, and the weight of surviving insects were recorded. Percent mortality and percent growth inhibition were calculated for each treatment. Percent growth inhibition (GI) was calculated as follows:

$$\% GI=[1-(TWIT/TNIT)/(TWIBC/TNIBC)]\times 100$$

where TWIT is the Total Weight of Insects in the Treatment,

TNIT is the Total Number of Insects in the Treatment

TWIBC is the Total Weight of Insects in the Background Check (Buffer control), and TNIBC is the Total Number of Insects in the Background Check (Buffer control).

The $GI_{50}$ was determined to be the concentration of chimeric DIG-152 protein in the diet at which the % GI value was 50. The $LC_{50}$ (50% Lethal Concentration) was recorded as the concentration of DIG-152 protein in the diet at which 50% of test insects were killed. Statistical analysis (One-way ANOVA) was done using JMP software (SAS, Cary, N.C.).

Table 2 presents the results of ingestion bioassays of DIG-152 protein on fall armyworm insect larvae.

TABLE 2

$GI_{50}$ and $LC_{50}$ values (in $ng/cm^2$) calculated from insect diet top loaded with DIG-152 protein.

| FAW | | rFAW | |
|---|---|---|---|
| $GI_{50}$ | $LC_{50}$ | $GI_{50}$ | $LC_{50}$ |
| 38.1 | 2828.7 | 78.9 | 2210.9 |

It is a feature of the DIG-152 protein of the subject invention that the growth of neonate larvae of fall armyworm (*Spodoptera frugiperda*) is inhibited following ingestion of the DIG-152 protein. Further, fall armyworm larvae that are resistant to intoxication by Cry1Fa are as susceptible to DIG-152 activity as are wild-type fall armyworm larvae. The significance of the susceptibility of these Cry1Fa resistant insects to Cry1Ca is discussed in more detail above.

EXAMPLE 4

Design of a Maize-Codon-Optimized Sequence Encoding the DIG-109 Protein

One skilled in the art of plant molecular biology will understand that multiple DNA sequences may be designed to encode a single amino acid sequence. A common means of increasing the expression of a coding region for a protein of interest is to tailor the coding region in such a manner that its codon composition resembles the overall codon composition of the host in which the gene is destined to be expressed. Guidance regarding the design and production of synthetic genes can be found in, for example, WO 1997/13402 and U.S. Pat. No. 5,380,831.

A DNA sequence having a maize codon bias was designed and synthesized to produce the DIG-109 chimeric insecticidal protein in transgenic monocot plants. A codon usage table for maize (*Zea mays* L.) was calculated from 706 protein coding sequences obtained from sequences deposited in GenBank (world wide web: ncbi.nlm.nih.gov). A weighted-average maize codon set was calculated after omitting any redundant codon used less than about 10% of total codon uses for that amino acid. The Weighted Average representation for each codon was calculated using the formula:

$$\text{Weighted Average \% of } C1=1/(\%\ C1+\%\ C2+\%\ C3+\text{etc.})\times\%\ C1\times 100$$

where C1 is the codon in question and % C2, % C3, etc. represent the average % usage values of the remaining synonymous codons.

To derive a maize-codon-optimized DNA sequence encoding the 1164 amino acid DIG-109 protein of SEQ ID NO:2, codon substitutions to the native cry1Ca DNA sequence encoding the Cry1Ca core toxin segment were made such that the resulting DNA sequence had the overall codon composition of the maize-optimized codon bias table. In similar fashion, codon substitutions to the native cry1Ab DNA sequence encoding the Cry1Ab protoxin segment were made such that the resulting DNA sequence had the overall codon composition of the maize-optimized codon bias table. Further refinements to the sequences were made to eliminate undesirable restriction enzyme recognition sites, potential plant intron splice sites, long runs of A/T or C/G residues, and other motifs that might interfere with RNA stability, transcription, or translation of the coding region in plant cells. Other changes were made to introduce desired restriction enzyme recognition sites, and to eliminate long internal Open Reading Frames (frames other than +1). These changes were all made within the constraints of retaining approximately the maize-biased codon composition. A complete maize-codon-optimized sequence (encoding the DIG-109 protein) is disclosed as SEQ ID NO:3. Synthesis of the DNA fragment was performed by a commercial vendor (DNA2.0, Menlo Park, Calif.).

EXAMPLE 5

Construction of Plant Transformation Vectors Containing Plant-Expressible Genes Encoding DIG-109 Proteins The *Agrobacterium* superbinary system (Japan Tobacco, Tokyo, JP) is conveniently used for transformation of monocot plant hosts. The superbinary system employs the pSB11 shuttle vector plasmid which contains the sequences for the Right T-DNA border repeat (RB) and Left T-DNA border repeat (LB) separated by multiple cloning sites. A derivative of pSB11 (called pDAB7691) was prepared by standard DNA cloning methods. Plasmid pDAB7691 contains the maize-optimized DIG-109 coding sequence (CDS; i.e., SEQ ID NO:3) under the transcriptional control of the maize ubiquitin1 promoter with associated intron1 (U.S. Pat. No. 5,510,474) and the maize Per5 3' Untranslated Region (3' UTR) (U.S. Pat. No. 7,179,902). Further, pDAB7691 contains a plant selectable marker gene comprising the Dow AgroSciences DSM2 CDS (WO 2008/070845 A2) under the transcriptional control of the rice actin1 promoter with associated intron1 (U.S. Pat. No. 5,641,876) and the maize Lipase 3' UTR (U.S. Pat. No. 7,179,902). The physical arrangement of the components of the pDAB7691 T-region is conveniently illustrated as:

RB>maize Ubi1 promoter:DIG-109 CDS:maize Per5 3'UTR>rice Act1 promoter:DSM2 CDS:maize Lip 3'UTR>LB A second derivative of pSB11 (called pDAB100276) was prepared by standard DNA cloning methods. Plasmid pDAB100276 contains the maize-optimized DIG-109 coding sequence (CDS; i.e., SEQ ID NO:3) under the transcriptional control of the maize ubiquitin1 promoter with associated intron1 and the maize Per5 3' UTR. Further, pDAB100276 contains a plant selectable marker gene comprising the Dow AgroSciences AAD1 CDS (US Patent Application No. 20090093366), under the transcriptional control of the maize ubiquitin1 promoter with associated intron1 and the maize Lipase 3' UTR. The physical arrangement of the components of the pDAB100276 T-region is conveniently illustrated as:

RB>maize Ubi1 promoter:DIG-109 CDS: maize Per5 3'UTR>maize Ubi1 promoter:AAD-1 CDS:maize Lip 3' UTR>LB To prepare for *Agrobacterium* transformation, cells of *Escherichia coli* cloning strain DH5α harboring plasmid pDAB7691 or plasmid pDAB100276 were grown at 37° overnight on LB agar medium (g/L: Bacto Tryptone, 10; Bacto Yeast Extract, 5; NaCl, 10; agar, 15) in containing Spectinomycin (100 μg/mL). Strain DH5α cells containing the conjugal mobilizing plasmid pRK2013 were grown on LB agar containing Kanamycin (50 μg/mL). After incubation the plates were placed at 4° to await the availability of the *Agrobacterium tumefaciens* strain LBA4404 containing plasmid pSB1.

EXAMPLE 6

*Agrobacterium* Transformation for Generation of Superbinary Vectors

The *Agrobacterium* superbinary system, which employs *Agrobacterium tumefaciens* strain LBA4404 containing plasmid pSB1, is conveniently used for transformation of monocot plant hosts. Methodologies for constructing and validating superbinary vectors are well established as provided in the Operating Manual for pSB1 (Japan Tobacco). Standard microbiological and molecular biological methods were used to generate and validate the superbinary plasmid pDAS5162, which is a cointegrant plasmid comprising plasmids pSB1 and pDAB7691, and superbinary plasmid pDAS5848, which is a cointegrant plasmid comprising plasmids pSB1 and pDAB100276.

EXAMPLE 7

Production of DIG-109 Protein in Maize Plants

*Agrobacterium*-Mediated Transformation of Maize

Seeds from a Hi-II F1 cross (Armstrong et al., 1991) were planted into 5-gallon-pots containing a mixture of 95%

Metro-Mix 360 soilless growing medium (Sun Gro Horticulture, Bellevue, Wash.) and 5% clay/loam soil. The plants were grown in a greenhouse using a combination of high pressure sodium and metal halide lamps with a 16 hr light:8 hr dark photoperiod. Controlled sib-pollinations were performed to obtain immature F2 embryos for transformation. Maize ears were harvested at approximately 8-10 days post-pollination when immature embryos were between 1.0 mm and 2.0 mm in size.

Infection and Co-Cultivation.

Maize ears were dehusked and surface sterilized by scrubbing with liquid soap, immersing in 20% commercial bleach (containing 5% sodium hypochlorite) for about 20 minutes, then rinsing three times with sterile water. A suspension of *Agrobacterium tumefaciens* cells containing pDAS5162, a superbinary vector harboring a gene encoding the DIG-109 protein and containing the DSM2 plant selectable marker gene, was prepared by transferring 1 or 2 loops of bacteria [grown for 2-3 days at 28° on YEP solid medium (g/L: Bacto Yeast Extract, 10; Bacto Peptone, 10; NaCl, 5; agar, 15) containing 100 mg/L Spectinomycin, 10 mg/L Tetracycline, and 250 mg/L Streptomycin] into 5 mL of liquid infection medium [LS Basal Medium (Linsmaier and Skoog, 1965), N6 vitamins (Chu et al., 1975), 1.5 mg/L 2,4-Dichlorophenoxyacetic acid (2,4-D), 68.5 g/L sucrose, 36.0 g/L glucose, 6 mM L-proline, pH 5.2] containing 100 μM acetosyringone.

Alternatively, a suspension of *Agrobacterium tumefaciens* cells containing pDAS5848, a superbinary vector harboring a gene encoding the DIG-109 protein and containing the AAD-1 plant selectable marker gene, was prepared by transferring 1 or 2 loops of bacteria grown as above into 5 mL of liquid infection medium containing 100 to 200 μM acetosyringone.

In both cases, the solution was vortexed until a uniform suspension was achieved, and the concentration was adjusted to a final density of 200 Klett units using a Klett-Summerson colorimeter with a purple filter (for pDAS5162 transformations), or to an optical density of 1.2 at 550 nm (for pDAS5848 transformations). Immature embryos were isolated directly into a microcentrifuge tube containing 2 mL of the infection medium. The medium was removed and replaced with 1 mL of the *Agrobacterium* solution and the *Agrobacterium*/embryo solution was incubated for 5 to 10 minutes at room temperature. Embryos were then transferred to cocultivation medium [LS Basal Medium, N6 vitamins, 1.5 mg/L 2,4-D, 30.0 g/L sucrose, 6 mM L-proline, 0.85 mg/L AgNO3, 2.8 g/L Gellan gum (PhytoTechnology Laboratories, Lenexa, Kans.), pH 5.8] containing 100 μM acetosyringone (for pDAS5162 transformants) or containing 100 to 200 μM acetosyringone (for pDAS5848 transformants), and cocultivated for 3-4 days at 20° in the dark.

After cocultivation, the embryos were transferred to resting medium containing MS salts and vitamins, 6 mM L-proline, 100 mg/L myo-inositol, 500 mg/L MES, 30 g/L sucrose, 1.5 mg/L 2,4-D, 0.85 mg/L $AgNO_3$, 250 mg/L Cefotaxime, 2.8 g/L Gellan gum, pH 5.8. Approximately 7 days later, embryos were transferred to the same medium supplemented with 3 mg/L Bialaphos (for pDAS5162 transformants) or supplemented with 100 nM haloxyfop (for pDAS5848 transformants) (selection medium). Transformed isolates were identified after approximately 8 weeks and were bulked up by transferring to fresh selection medium at 2-week intervals for regeneration and analysis.

Regeneration and Seed Production.

For regeneration, the cultures were transferred to “28” induction medium (MS salts and vitamins, 30 g/L sucrose, 5 mg/L Benzylaminopurine, 0.25 mg/L 2,4-D, 250 mg/L Cefotaxime, 2.5 g/L Gellan gum, pH 5.7) supplemented with 3 mg/L Bialaphos (for pDAS5162 transformants) or supplemented with 100 nM haloxyfop (for pDAS5848 transformants). Incubation was for 1 week under low-light conditions (14 $\mu Em^{-2}s^{-1}$), then 1 week under high-light conditions (approximately 89 $\mu Em^{-2}s^{-1}$). Tissues were subsequently transferred to “36” regeneration medium (same as induction medium except lacking plant growth regulators). When plantlets were 3-5 cm in length, they were transferred to glass culture tubes containing SHGA medium [(Schenk and Hildebrandt (1972) salts and vitamins; PhytoTechnologies Labr.), 1.0 g/L myo-inositol, 10 g/L sucrose and 2.0 g/L Gellan gum, pH 5.8] to allow for further growth and development of the shoot and roots. Plants were transplanted to the same soil mixture as described earlier and grown to flowering in the greenhouse. Controlled pollinations for seed production were conducted.

Those skilled in the art of maize transformation will understand that other methods are available for maize transformation and for selection of transformed plants when other plant expressible selectable marker genes (e.g. herbicide tolerance genes) are used.

EXAMPLE 8

Biochemical Analysis and Insect Bioassays of Maize Plants Producing DIG-109 Protein The production of DIG-109 protein in transgenic maize plants was examined in proteins extracted from leaves of young plants (T0 generation). Two 6 mm diameter maize leaf disks were placed in a sample tube from a deep well 96 cluster tube box (Costar Cat#3957) and frozen at −80° until day of analysis. At that time, two 4.5 mm zinc-coated Daisy™ BB’s were added to each (frozen) tube, along with 200 μL of extraction buffer comprised of PBS (Phosphate Buffered Saline; Fisher Cat# BP665-1) plus 0.05% Tween 20. Each tube was capped and the box was placed in a bead mill (Kleco™ 4-96 Pulverizer; Garcia Manufacturing, Visalia, Calif.) at maximum setting for three minutes. The pulverized samples were centrifuged for 5 minutes at 2,500×g and the supernatant containing soluble proteins was used in the immunoassays.

Immunoblot analyses of extracted maize leaf proteins revealed that the DIG152RPC1 polyclonal antibody (prepared from rabbits immunized with the trypsin-activated Cry1Ca core toxin protein) does not cross react with proteins extracted from leaves of nontransgenic plants. In extracts of plants transformed with pDAS5162, several protein species were detected by the DIG152PRC1 antibody.

It is apparent that, although the transgene introduced into maize via transformation with pDAS5162 encodes the full-length DIG-109 protein, proteolytic activity within the maize cells processes the nascent protein to an abundance of stable smaller molecular weight species.

The insect toxicity of leaves harvested from independently isolated transgenic maize plants transformed with the pDAS5162 construct was tested in vitro using neonate larvae of fall armyworm (FAW, *Spodoptera frugiperda* (J. E. Smith)) and Cry1F-resistant FAW (rFAW) larvae. FAW eggs were obtained from a commercial insectary (Benzon), and rFAW eggs came from a non-commercial population (Dow AgroSciences). Leaf segment samples were taken for insect bioassays from greenhouse-grown T0 plants approximately 2 weeks after the plants were transplanted from the laboratory into the greenhouse. Two leaf pieces from each plant (each approximately 1 square inch) were placed into separate wells of a 32-well tray (CD International) on top of about 3 mL of solidified 2% agar. Eggs were hatched onto multi-species Lepidopteran diet (Southland Products) and neonate larvae were selected when less than 24 hours old. Approximately 10 larvae per leaf segment were carefully placed into each well using a camel hair paintbrush. Infested trays were sealed with the perforated lids supplied with the trays, then held at 28°, 40% RH, 16 hr light:8 hr dark for three days. Percent damage (% DAM) for each leaf piece was recorded at the conclusion of the test. Damage ratings were averaged and used to determine which plants had the least damage from each type of test insect. Tests were replicated several times for all insects.

Data were analyzed using JMP statistical software (SAS, Cary, N.C.), averaging the % DAM scores for each plant, for each insect type. The "Fit Y by X" model was used for one way ANOVA analyses. Tukey-Kramer means separation was used as needed to analyze for significant differences amongst the mean % DAM scores for each treatment. Comparisons were made to the % DAM scores obtained from control plants of similar age. Positive control plants were grown from seeds of the commercial HERCULEX I™ hybrid, which produces the Cry1Fa B.t. toxin. Negative controls (i.e. nontransformed plants) were represented by the Hi II and B 104 lines, and a HERCULEX I™ Isoline (a non-Cry containing parent of the HERCULEX I™ hybrid).

FIG. 1 summarizes the results obtained in such insect bioassay tests. It is a surprising finding that there is a positive correlation between the production of DIG-109 in the transgenic leaves and the % DAM rating. For FAW, F=35.3; d.f.=1, 33; P<0.0001; $r^2$=0.52, and for rFAW, F=25.3; d.f.=1, 33; P<0.0001; $r^2$=0.43. It is a further surprising and novel finding that fall armyworm larvae that are resistant to intoxication by the Cry1Fa B.t. toxin are yet inhibited from feeding by the DIG-109 B.t. toxin.

It is understood that other insect pests of maize may be tested in similar fashion. These pests include, but are not limited to: *Agromyza parvicornis* (corn blot leafminer), *Agrotis ipsilon* (black cutworm), *Anticarsia gemmatalis* (velvetbean caterpillar), *Diatraea grandiosella* (southwestern corn borer), *Diatraea saccharalis* (sugarcane borer), *Elasmopalpus lignosellus* (lesser cornstalk borer), *Helicoverpa zea* (corn earworm), *Heliothis virescens*, (tobacco budworm), *Ostrinia nubilalis* (European corn borer), Cry1F-resistant *O. nubilalis, Plutella xylostella* (diamondback moth), Cry1-resistant *P. xylostella, Spodoptera exigua* (beet armyworm), and *Trichoplusia ni* (cabbage looper).

Transgenic maize plants transformed with pDAS5848 (T0 generation) were also examined by insect bioassay and by immunoanalyses. The amount of DIG-109 protein in leaf extracts was quantitated using a commercially available Cry1C ELISA detection kit (Envirologix™, Portland, Mass.; Cat# AP007), and the level of DIG-109 protein detected was expressed as parts per million (ppm; 1 ppm represents 1 ng of DIG-109 protein per mg of total soluble protein in the extract).

Feeding damage by FAW and rFAW was codified as follows: 0=no damage or a few pinhole feeding marks, 1=25% to 50% of leaf eaten, and 2=most all of leaf consumed or no leaf left. A protected plant is one whose damage score is 0.67 or lower.

The data in Table 3 show that there is a positive correlation between the presence of DIG-109 protein species detected by ELISA in the T0 plants and control of feeding damage done by fall armyworm larvae in in vitro bioassays. The plant with the highest detected level of DIG-109 protein (plant 5848-005.4) had the lowest leaf feeding damage score. Leaves from plants with lower levels of detectable DIG-109 protein in the range of 190 to 230 ppm also suffered less feeding damage than was seen with leaves from the negative control plants (i.e. nontransformed controls B104 and Hi II), which had mean damage scores of 1.7 and 1.8. In all pDAS5848 leaves examined, the predominant DIG-109 protein species detected comprised a doublet of peptides of approximate size 60 kDa and 55 kDa.

TABLE 3

Levels of DIG-109 protein in pDAS5848-transformed transgenic maize leaf extracts and reduction of fall armyworm feeding damage.

| Plant Identifier | DIG-109 ppm | FAW Damage |
|---|---|---|
| 5848-005.4 | 680 | 0 |
| 5848-008.4 | 230 | 0.67 |
| 5848-001.3 | 220 | 1 |
| 5848-001.1 | 210 | 1 |
| 5848-001.2 | 190 | 0.33 |
| 5848-003.1 | 190 | 1 |
| 5848-003.2 | 190 | 0.67 |
| 5848-003.3 | 190 | 0.67 |
| **Control Plants (Number Tested)** | **DIG-109 ppm** | **FAW Damage ($SD^b$)** |
| B104 (19) | NA[a] | 1.8 (0.5) |
| Hi II (20) | NA | 1.7 (0.5) |
| Herculex I ™ (20) | NA | 0.5 (0.6) |

[a]NA = Not Applicable;
[b]SD = Standard Deviation of the mean

It is thus a feature of the subject invention that the DIG-109 protein, when produced in maize plants, renders the plants resistant to feeding damage by fall armyworm larvae and Cry1F-resistant fall armyworm larvae.

EXAMPLE 9

Competitive Binding Experiments of Cry1Fa and Cry1Ca Core Toxin Proteins with Isolated Brush Border Membrane Vesicles of *Spodoptera frugiperda*

The following Examples evaluate the competition binding of Cry1 core toxin proteins to putative receptors in insect gut tissues. It is shown that 125I-labeled Cry1Ca core toxin protein binds with high affinity to Brush Border Membrane Vesicles (BBMV's) prepared from *Spodoptera frugiperda* (fall armyworm) and that Cry1Fa core toxin protein does not compete with this binding.

Purification of Cry Proteins.

A gene encoding a chimeric protein comprising the Cry1Ca core toxin and Cry1Ab protoxin was expressed in the *Pseudomonas fluorescens* expression strain as described in Example 2. In similar fashion, a gene encoding a chimeric protein, comprising the Cry1Fa core toxin (603 amino acids) and Cry1Ab protoxin (545 amino acids) was expressed in the Pf system. The proteins were purified by the methods of Example 2, and trypsin digestion to produce activated core toxins from the full-length proteins was performed and the products were purified by the methods of Example 2.

Preparations of the trypsin processed (activated core toxin) proteins were >95% pure and had a molecular weight of approximately 65 kDa as determined experimentally by SDS-PAGE.

Standard methods of protein quantification and SDS-polyacrylamide gel electrophoresis were employed as taught, for example, in Sambrook et al. (1989) and Ausubel et al. (1995), and updates thereof.

Preparation and Fractionation of Solubilized BBMV's.

Last instar *Spodoptera frugiperda* larvae were fasted overnight and then dissected after chilling on ice for 15 minutes. The midgut tissue was removed from the body cavity, leaving behind the hindgut attached to the integument. The midgut was placed in a 9× volume of ice cold homogenization buffer (300 mM mannitol, 5 mM EGTA, 17 mM Tris base, pH7.5), supplemented with Protease Inhibitor Cocktail (Sigma-Aldrich P-2714) diluted as recommended by the supplier. The tissue was homogenized with 15 strokes of a glass tissue homogenizer. BBMV's were prepared by the $MgCl_2$ precipitation method of Wolfersberger (1993). Briefly, an equal volume of a 24 mM $MgCl_2$ solution in 300 mM mannitol was mixed with the midgut homogenate, stirred for 5 minutes and allowed to stand on ice for 15 min. The solution was centrifuged at 2,500×g for 15 min at 4°. The supernatant was saved and the pellet suspended into the original volume of 0.5× diluted homogenization buffer and centrifuged again. The two supernatants were combined and centrifuged at 27,000×g for 30 min at 4° to form the BBMV fraction. The pellet was suspended into BBMV Storage Buffer (10 mM HEPES, 130 mM KCl, 10% glycerol, pH7.4) to a protein concentration of about 3 mg/mL. Protein concentration was determined using Bovine Serum Albumin (BSA) as the standard. Alkaline phosphatase determination (a marker enzyme for the BBMV fraction) was made prior to freezing the samples using the QuantiChrom™ DALP-250 Alkaline Phosphatase Assay Kit (Gentaur Molecular Products, Kampenhout, BE) following the manufacturer's instructions. The specific activity of this enzyme typically increased 7-fold compared to that found in the starting midgut homogenate fraction. The BBMV's were aliquoted into 250 μL samples, flash frozen in liquid nitrogen and stored at −80°.

Electrophoresis.

Analysis of proteins by SDS-PAGE was conducted under reducing (i.e. in 5% β-mercaptoethanol, BME) and denaturing (i.e. heated 5 minutes at 90° in the presence of 2% SDS) conditions. Proteins were loaded into wells of a 4% to 20% Tris-Glycine polyacrylamide gel (BioRad; Hercules, Calif.) and separated at 200 volts for 60 minutes. Protein bands were detected by staining with Coomassie Brilliant Blue R-250 (BioRad) for one hour, and destained with a solution of 5% methanol in 7% acetic acid. The gels were imaged and analyzed using a BioRad Fluoro-S Multi Imager™. Relative molecular weights of the protein bands were determined by comparison to the mobilities of known molecular weight proteins observed in a sample of BenchMark™ Protein Ladder (Life Technologies, Rockville, Md.) loaded into one well of the gel.

Iodination of Cry1Ca Core Toxin Protein.

Purified Cry1Ca core toxin protein was iodinated using Pierce Iodination Beads (Thermo Fisher Scientific, Rockford, Ill.). Briefly, two Iodination Beads were washed twice with 500 μL of PBS (20 mM sodium phosphate, 0.15 M NaCl, pH7.5), and placed into a 1.5 mL centrifuge tube with 100 μL of PBS. 0.5 mCi of 125I-labeled sodium iodide was added, the components were allowed to react for 5 minutes at room temperature, then 1 μg of Cry1Ca core toxin protein was added to the solution and allowed to react for an additional 3 to 5 minutes. The reaction was terminated by pipetting the solution from the Iodination Beads and applying it to a Zeba™ spin column (Invitrogen) equilibrated in 50 mM CAPS, pH10.0, 1 mM DTT (dithiothreitol), 1 mM EDTA, and 5% glycerol. The Iodination Beads were washed twice with 10 μL of PBS and the wash solution was also applied to the Zeba™ desalting column. The radioactive solution was eluted through the spin column by centrifuging at 1,000×g for 2 min. 125I-radiolabeled Cry1Ca core toxin protein was then dialyzed against 50 mM CAPS, pH10.0, 1 mM DTT, 1 mM EDTA, and 5% glycerol.

Imaging.

Radio-purity of the iodinated Cry1Ca core toxin protein was determined by SDS-PAGE and phosphorimaging. Briefly, SDS-PAGE gels were dried using a BioRad gel drying apparatus following the manufacturer's instructions. The dried gels were imaged by wrapping them in Mylar film (12 μm thick) and exposing them under a Molecular Dynamics storage phosphor screen (35 cm×43 cm) for 1 hour. The plates were developed using a Molecular Dynamics Storm 820 phosphorimager and the image was analyzed using ImageQuant™ software.

EXAMPLE 10

Binding of 125I-Labeled Cry1 Core Toxin Protein to BBMV's from *Spodoptera frugiperda*

A saturation curve was generated using 125I-radiolabeled Cry1Ac core toxin protein to determine the optimal amount of BBMV protein to use in the binding assays with Cry1Ca and Cry1Fa core toxin proteins. 0.5 nM of 125I-radiolabeled Cry1Ac core toxin protein was incubated for 1 hr at 28° in binding buffer (8 mM $NaHPO_4$, 2 mM $KH_2PO_4$, 150 mM NaCl, 0.1% BSA, pH7.4) with amounts of BBMV protein ranging from 0 μg/mL to 500 μg/mL (total volume of 0.5 mL). 125I-labeled Cry1Ac core toxin protein bound to the BBMV proteins was separated from the unbound fraction by sampling 150 μL of the reaction mixture in triplicate into separate 1.5 mL centrifuge tubes and centrifuging the samples at 14,000×g for 8 minutes at room temperature. The supernatant was gently removed and the pellet was washed three times with ice cold binding buffer. The bottom of the centrifuge tube containing the pellet was cut off, placed into a 13×75 mm glass culture tube and the samples were counted for 5 minutes each in the gamma counter. CPM (counts per minute) obtained minus background CPM (reaction with no BBMV protein) was plotted versus BBMV protein concentration. In accordance with other results as well, the optimal concentration of BBMV protein to use in the binding assays was determined to be 150 μg/mL.

EXAMPLE 11

Competitive Binding Assays to BBMVs from *S. frugiperda* with Core Toxin Proteins of Cry1Ca and Cry1Fa Homologous and heterologous competition binding assays were conducted using 150 μg/mL BBMV protein and 0.5 nM of the 125I-radiolabeled Cry1Ca core toxin protein. Concentrations of the competitive non-radiolabeled Cry1Fa core toxin protein added to the reaction mixture ranged from 0.045 nM to 1000 nM and were added at the same time as the radioactive Cry1Ca core toxin protein, to assure true binding competition. Incubations were carried out for 1 hr at 28° and the amount of 125I-labeled Cry1Ca core toxin protein bound to the BBMV (specific binding) was measured as described above. Non-specific binding was represented by the counts obtained in the presence of 1,000 nM of non-radiolabeled Cry1Ca core toxin protein. One hundred percent total binding was considered to be the amount of binding in the absence of any competitor Cry1Fa core toxin protein.

Receptor binding assays using 125I-labeled Cry1Ca core toxin protein determined the ability of the Cry1Fa core toxin protein to displace this radiolabeled ligand from its binding site on BBMV's from *S. frugiperda*. The results (FIG. 2) show that the Cry1Fa core toxin protein did not displace bound 125I-labeled Cry1Ca core toxin protein from its receptor protein(s) at concentrations as high as 300 nM (600 times the concentration of the radioactive binding ligand). As expected, unlabeled Cry1Ca core toxin protein was able to displace radiolabeled Cry1Ca core toxin protein from its binding protein(s), exhibiting a sigmoidal dose response curve with 50% displacement occurring at 5 nM.

It is thus indicated that the Cry1Ca core toxin protein interacts with a binding site in *S. frugiperda* BBMV that does not bind the Cry1Fa core toxin protein.

Figure 2:
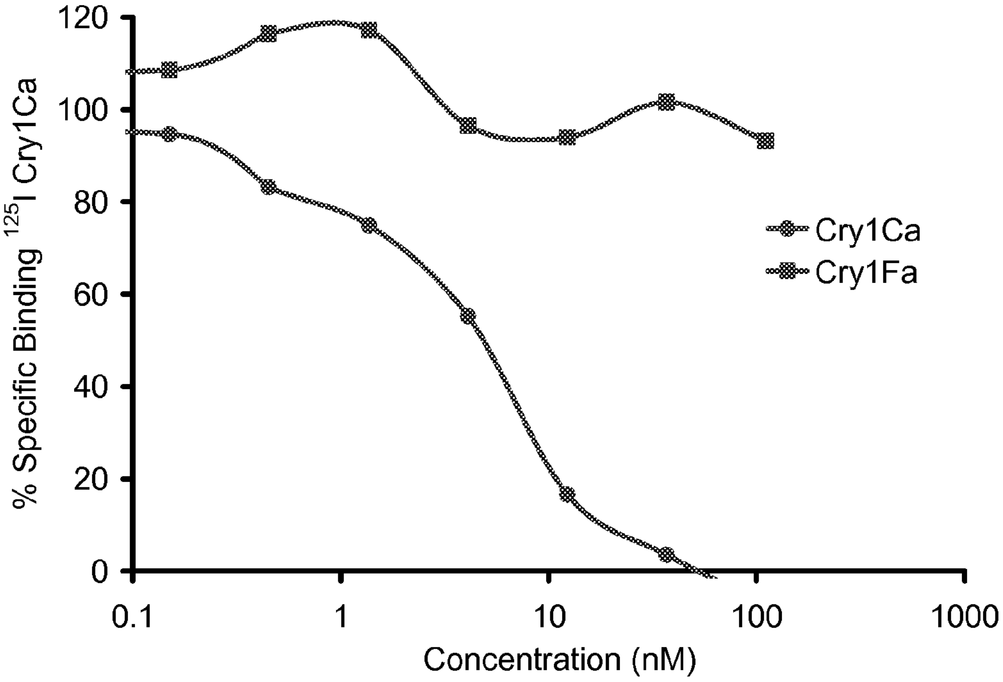
FIG. 2: Competition for binding to *Spodoptera frugiperda* BBMV's by Cry1Fa core toxin, Cry1Ca core toxin, and 125I-labeled Cry1Ca core toxin.

See FIG. 2: Competition for binding to *Spodoptera frugiperda* BBMV's by Cry1Fa core toxin, Cry1Ca core toxin, and 125I-labeled Cry1Ca core toxin.

EXAMPLE 12

Competitive Binding of Cry1Ca Core Toxin Protein and Biotin-Labeled Cry1Fa Core Toxin Protein to BBMVs of *Diatraea saccharalis*

The following Examples evaluate the competition binding of Cry1 core toxin proteins to putative receptors in insect gut tissues. It is shown that biotin-labeled Cry1Fa core toxin protein binds with high affinity to Brush Border Membrane Vesicles (BBMV's) prepared from *Diatraea saccharalis* (sugarcane borer) and that Cry1Ca core toxin protein does not compete with this binding.

Preparation and Fractionation of Solubilized BBMV's.

Last instar *D. saccharalis* larvae were fasted overnight and then dissected after chilling on ice for 15 minutes. BBMV preparations were made following the methods disclosed in Example 10.

Competition binding assay results using 125I-labeled Cry1Fa core toxin protein may have limited biological relevance, since iodination of Cry1Fa protein renders the protein inactive in insect feeding bioassays. In contrast, it has been discovered that biotinylated Cry1Fa core toxin protein retains its toxicity against insects. Further, it is possible to measure the interaction of this (biotinylated) protein with receptors in the presence of non-biotinylated (competing) Cry core toxin proteins. Such a competition experiment can detect binding of biotin-labeled Cry1Fa core toxin protein to receptors in *D. saccharalis* BBMV after electrophoresis of the BBMV proteins and transfer of the entire sample to a PVDF (polyvinylidene fluoride) membrane. Avidin conjugated to horseradish peroxidase, in combination with an enhanced chemical luminescence reagent, is used to visualize the biotin-labeled Cry1Fa core toxin protein.

Cry1Fa core toxin protein was labeled with biotin using a Pierce EZ-Link® Sulfo-NHS-LC Biotinylation Kit (Thermo Fisher Scientific). Briefly, 40 μL of Sulfo-NHS-LC-biotin (10 mg/mL in Dimethyl Sulfoxide) was added to 500 μL of Cry1Fa core toxin protein (2.0 mg/mL) in 0.1M sodium phosphate buffer, pH7.2. The reaction was incubated at 4° overnight, then unreacted Sulfo-NHS-LC-biotin was removed using a Zeba™ desalting column. Biotin incorporation into Cry1Fa core toxin protein was measured using the Pierce HABA-avidin displacement assay (Thermo Fisher Scientific) as described by the manufacturer.

Biotin labeled Cry1Fa core toxin protein (2.5 nM) was incubated 1 hr. at 28° with 0.2 mg of BBMV's prepared from *D. saccharalis* [in a total volume of 1.0 mL] in the presence or absence of a 500-fold excess of nonlabeled Cry1Fa or Cry1Ca core toxin proteins. Unbound biotin-labeled Cry1Fa core toxin protein was removed by centrifugation at 16,000×g for 10 min and the resulting pellet was washed 3 times with ice cold binding buffer. The pellet was suspended into 15 μL of 4× Laemmli sample buffer, vortexed and sonicated to assure complete solubilization, and heated to 90° for 3 min. The entire sample was loaded onto a 4% to 20% Tris glycine gel, separated by SDS-PAGE, and electro transferred onto PVDF membrane as recommended by the supplier's instructions (BioRad). 1,000 ng of Cry1Fa core toxin protein and Cry1Ca core toxin protein were also run on the gel as negative controls. Biotin-labeled Cry1Fa core toxin protein was visualized with avidin-conjugated horseradish peroxidase at 1:15,000 dilution with enhanced chemiluminescence using a 1:1 mixture of SuperSignal® West Pico Peroxide Solution with Luminal Enhancer Solution (Thermo Fisher Scientific, Catalog numbers 1859674 and 1859675). Bands were recorded using a Biorad Fluor-S MultiImager with Quantity One v.4.5.2 software.

The results demonstrated the detection of biotin-labeled Cry1Fa core toxin protein bound to receptors in *D. saccharalis* BBMV, and further showed that non-biotinylated Cry1Fa core toxin protein at 500-fold excess concentration completely displaced the bound biotinylated Cry1Fa core toxin protein from its receptor(s). In contrast, a 500-fold excess concentration of Cry1Ca core toxin protein was not able to displace the bound biotinylated Cry1Fa core toxin protein, indicating that Cry1Ca core toxin protein does not compete for the Cry1Fa core toxin protein binding site(s) in *D. saccharalis* BBMV. It is thus indicated that, analogous to the results obtained with BBMVs of *S. frugiperda*, the Cry1Fa core toxin protein and Cry1Ca core toxin protein bind to separate binding sites in *D. saccharalis* BBMVs.

REFERENCES

Finney, D. J. 1971. Probit analysis. Cambridge University Press, England.

Hua, G., L. Masson, J. L. Jurat-Fuentes, G. Schwab, and M. J. Adang. Binding analyses of *Bacillus thuringiensis* Cry d-endotoxins using brush border membrane vesicles of *Ostrinia nubilalis*. Applied and Environmental Microbiology 67[2], 872-879. 2001.

LeOra Software. 1987. POLO-PC. A user's guide to probit and logit analysis. Berkeley, Calif.

McGaughey, W. H., F. Gould, and W. Gelernter. Bt resistance management. Nature Biotechnology 16[2], 144-146. 1998

Marçon, P. R. G. C., L. J. Young, K. Steffey, and B. D. Siegfried. 1999. Baseline susceptibility of the European corn borer, *Ostrinia nubilalis* (Hübner) (Lepidoptera: Pyralidae) to *Bacillus thuringiensis* toxins. J. Econ. Entomol. 92 (2): 280-285.

Robertson, L. J. and H. K. Preisler. 1992. Pesticide bioassays with arthropods. CRC Press, Boca Ranton, Fla.

SAS Institute Inc. 1988. SAS procedures guide, Release 6.03 edition. SAS Institute Inc, Cary, N.C.

Stone, B. F. 1968. A formula for determining degree of dominance in cases of monofactorial inheritance of resistance to chemicals. Bull. WHO 38:325-329.

Van Mellaert, H., J. Botterman, J. Van Rie, and H. Joos. Transgenic plants for the prevention of development of insects resistant to *Bacillus thuringiensis* toxins. (Plant Genetic Systems N.V., Belg. 89-401499[400246], 57-19901205. EP. 5-31-1989

APPENDIX A

List of delta-endotoxins - from Crickmore et al. website (cited in application)
Accession Number is to NCBI entry (if available)

| Name | Acc No. | Authors | Year | Source Strain | Comment |
|---|---|---|---|---|---|
| Cry1Aa1 | AAA22353 | Schnepf et al | 1985 | Bt kurstaki HD1 | |
| Cry1Aa2 | AAA22552 | Shibano et al | 1985 | Bt sotto | |
| Cry1Aa3 | BAA00257 | Shimizu et al | 1988 | Bt aizawai IPL7 | |
| Cry1Aa4 | CAA31886 | Masson et al | 1989 | Bt entomocidus | |
| Cry1Aa5 | BAA04468 | Udayasuriyan et al | 1994 | Bt Fu-2-7 | |
| Cry1Aa6 | AAA86265 | Masson et al | 1994 | Bt kurstaki NRD-12 | |
| Cry1Aa7 | AAD46139 | Osman et al | 1999 | Bt C12 | |
| Cry1Aa8 | I26149 | Liu | 1996 | | DNA sequence only |
| Cry1Aa9 | BAA77213 | Nagamatsu et al | 1999 | Bt dendrolimus T84A1 | |
| Cry1Aa10 | AAD55382 | Hou and Chen | 1999 | Bt kurstaki HD-1-02 | |
| Cry1Aa11 | CAA70856 | Tounsi et al | 1999 | Bt kurstaki | |
| Cry1Aa12 | AAP80146 | Yao et al | 2001 | Bt Ly30 | |
| Cry1Aa13 | AAM44305 | Zhong et al | 2002 | Bt sotto | |
| Cry1Aa14 | AAP40639 | Ren et al | 2002 | unpublished | |
| Cry1Aa15 | AAY66993 | Sauka et al | 2005 | Bt INTA Mol-12 | |
| Cry1Ab1 | AAA22330 | Wabiko et al | 1986 | Bt berliner 1715 | |
| Cry1Ab2 | AAA22613 | Thorne et al | 1986 | Bt kurstaki | |
| Cry1Ab3 | AAA22561 | Geiser et al | 1986 | Bt kurstaki HD1 | |
| Cry1Ab4 | BAA00071 | Kondo et al | 1987 | Bt kurstaki HD1 | |
| Cry1Ab5 | CAA28405 | Hofte et al | 1986 | Bt berliner 1715 | |
| Cry1Ab6 | AAA22420 | Hefford et al | 1987 | Bt kurstaki NRD-12 | |
| Cry1Ab7 | CAA31620 | Haider & Ellar | 1988 | Bt aizawai IC1 | |
| Cry1Ab8 | AAA22551 | Oeda et al | 1987 | Bt aizawai IPL7 | |
| Cry1Ab9 | CAA38701 | Chak & Jen | 1993 | Bt aizawai HD133 | |
| Cry1Ab10 | A29125 | Fischhoff et al | 1987 | Bt kurstaki HD1 | |
| Cry1Ab11 | I12419 | Ely & Tippett | 1995 | Bt A20 | DNA sequence only |
| Cry1Ab12 | AAC64003 | Silva-Werneck et al | 1998 | Bt kurstaki S93 | |
| Cry1Ab13 | AAN76494 | Tan et al | 2002 | Bt c005 | |
| Cry1Ab14 | AAG16877 | Meza-Basso & Theoduloz | 2000 | Native Chilean Bt | |
| Cry1Ab15 | AAO13302 | Li et al | 2001 | Bt B-Hm-16 | |
| Cry1Ab16 | AAK55546 | Yu et al | 2002 | Bt AC-11 | |
| Cry1Ab17 | AAT46415 | Huang et al | 2004 | Bt WB9 | |
| Cry1Ab18 | AAQ88259 | Stobdan et al | 2004 | Bt | |
| Cry1Ab19 | AAW31761 | Zhong et al | 2005 | Bt X-2 | |
| Cry1Ab20 | ABB72460 | Liu et al | 2006 | BtC008 | |
| Cry1Ab21 | ABS18384 | Swiecicka et al | 2007 | Bt IS5056 | |
| Cry1Ab22 | ABW87320 | Wu and Feng | 2008 | BtS2491Ab | |
| Cry1Ab-like | AAK14336 | Nagarathinam et al | 2001 | Bt kunthala RX24 | uncertain sequence |
| Cry1Ab-like | AAK14337 | Nagarathinam et al | 2001 | Bt kunthala RX28 | uncertain sequence |
| Cry1Ab-like | AAK14338 | Nagarathinam et al | 2001 | Bt kunthala RX27 | uncertain sequence |
| Cry1Ab-like | ABG88858 | Lin et al | 2006 | Bt ly4a3 | insufficient sequence |
| Cry1Ac1 | AAA22331 | Adang et al | 1985 | Bt kurstaki HD73 | |
| Cry1Ac2 | AAA22338 | Von Tersch et al | 1991 | Bt kenyae | |
| Cry1Ac3 | CAA38098 | Dardenne et al | 1990 | Bt BTS89A | |
| Cry1Ac4 | AAA73077 | Feitelson | 1991 | Bt kurstaki PS85A1 | |
| Cry1Ac5 | AAA22339 | Feitelson | 1992 | Bt kurstaki PS81GG | |
| Cry1Ac6 | AAA86266 | Masson et al | 1994 | Bt kurstaki NRD-12 | |
| Cry1Ac7 | AAB46989 | Herrera et al | 1994 | Bt kurstaki HD73 | |
| Cry1Ac8 | AAC44841 | Omolo et al | 1997 | Bt kurstaki HD73 | |
| Cry1Ac9 | AAB49768 | Gleave et al | 1992 | Bt DSIR732 | |
| Cry1Ac10 | CAA05505 | Sun | 1997 | Bt kurstaki YBT-1520 | |
| Cry1Ac11 | CAA10270 | Makhdoom & Riazuddin | 1998 | | |
| Cry1Ac12 | I12418 | Ely & Tippett | 1995 | Bt A20 | DNA sequence only |
| Cry1Ac13 | AAD38701 | Qiao et al | 1999 | Bt kurstaki HD1 | |

APPENDIX A-continued

List of delta-endotoxins - from Crickmore et al. website (cited in application)
Accession Number is to NCBI entry (if available)

| | | | | | |
|---|---|---|---|---|---|
| Cry1Ac14 | AAQ06607 | Yao et al | 2002 | Bt Ly30 | |
| Cry1Ac15 | AAN07788 | Tzeng et al | 2001 | Bt from Taiwan | |
| Cry1Ac16 | AAU87037 | Zhao et al | 2005 | Bt H3 | |
| Cry1Ac17 | AAX18704 | Hire et al | 2005 | Bt kenyae HD549 | |
| Cry1Ac18 | AAY88347 | Kaur & Allam | 2005 | Bt SK-729 | |
| Cry1Ac19 | ABD37053 | Gao et al | 2005 | Bt C-33 | |
| Cry1Ac20 | ABB89046 | Tan et al | 2005 | | |
| Cry1Ac21 | AAY66992 | Sauka et al | 2005 | INTA Mol-12 | |
| Cry1Ac22 | ABZ01836 | Zhang & Fang | 2008 | Bt W015-1 | |
| Cry1Ac23 | CAQ30431 | Kashyap et al | 2008 | Bt | |
| Cry1Ac24 | ABL01535 | Arango et al | 2008 | Bt 146-158-01 | |
| Cry1Ac25 | FJ513324 | Guan Peng et al | 2008 | Bt Tm37-6 | No NCBI link July 09 |
| Cry1Ac26 | FJ617446 | Guan Peng et al | 2009 | Bt Tm41-4 | No NCBI link July 09 |
| Cry1Ac27 | FJ617447 | Guan Peng et al | 2009 | Bt Tm44-1B | No NCBI link July 09 |
| Cry1Ac28 | ACM90319 | Li et al | 2009 | Bt Q-12 | |
| Cry1Ad1 | AAA22340 | Feitelson | 1993 | Bt aizawai PS81I | |
| Cry1Ad2 | CAA01880 | Anonymous | 1995 | Bt PS81RR1 | |
| Cry1Ae1 | AAA22410 | Lee & Aronson | 1991 | Bt alesti | |
| Cry1Af1 | AAB82749 | Kang et al | 1997 | Bt NT0423 | |
| Cry1Ag1 | AAD46137 | Mustafa | 1999 | | |
| Cry1Ah1 | AAQ14326 | Tan et al | 2000 | | |
| Cry1Ah2 | ABB76664 | Qi et al | 2005 | Bt alesti | |
| Cry1Ai1 | AAO39719 | Wang et al | 2002 | | |
| Cry1A-like | AAK14339 | Nagarathinam et al | 2001 | Bt kunthala nags3 | uncertain sequence |
| Cry1Ba1 | CAA29898 | Brizzard & Whiteley | 1988 | Bt thuringiensis HD2 | |
| Cry1Ba2 | CAA65003 | Soetaert | 1996 | Bt entomocidus HD110 | |
| Cry1Ba3 | AAK63251 | Zhang et al | 2001 | | |
| Cry1Ba4 | AAK51084 | Nathan et al | 2001 | Bt entomocidus HD9 | |
| Cry1Ba5 | ABO20894 | Song et al | 2007 | Bt sfw-12 | |
| Cry1Ba6 | ABL60921 | Martins et al | 2006 | Bt S601 | |
| Cry1Bb1 | AAA22344 | Donovan et al | 1994 | Bt EG5847 | |
| Cry1Bc1 | CAA86568 | Bishop et al | 1994 | Bt morrisoni | |
| Cry1Bd1 | AAD10292 | Kuo et al | 2000 | Bt wuhanensis HD525 | |
| Cry1Bd2 | AAM93496 | Isakova et al | 2002 | Bt 834 | |
| Cry1Be1 | AAC32850 | Payne et al | 1998 | Bt PS158C2 | |
| Cry1Be2 | AAQ52387 | Baum et al | 2003 | | |
| Cry1Be3 | FJ716102 | Xiaodong Sun et al | 2009 | Bt | No NCBI link July 09 |
| Cry1Bf1 | CAC50778 | Arnaut et al | 2001 | | |
| Cry1Bf2 | AAQ52380 | Baum et al | 2003 | | |
| Cry1Bg1 | AAO39720 | Wang et al | 2002 | | |
| Cry1Ca1 | CAA30396 | Honee et al | 1988 | Bt entomocidus 60.5 | |
| Cry1Ca2 | CAA31951 | Sanchis et al | 1989 | Bt aizawai 7.29 | |
| Cry1Ca3 | AAA22343 | Feitelson | 1993 | Bt aizawai PS81I | |
| Cry1Ca4 | CAA01886 | Van Mellaert et al | 1990 | Bt entomocidus HD110 | |
| Cry1Ca5 | CAA65457 | Strizhov | 1996 | Bt aizawai 7.29 | |
| Cry1Ca6 | AAF37224 | Yu et al | 2000 | Bt AF-2 | |
| Cry1Ca7 | AAG50438 | Aixing et al | 2000 | Bt J8 | |
| Cry1Ca8 | AAM00264 | Chen et al | 2001 | Bt c002 | |
| Cry1Ca9 | AAL79362 | Kao et al | 2003 | Bt G10-01A | |
| Cry1Ca10 | AAN16462 | Lin et al | 2003 | Bt E05-20a | |
| Cry1Ca11 | AAX53094 | Cai et al | 2005 | Bt C-33 | |
| Cry1Cb1 | M97880 | Kalman et al | 1993 | Bt galleriae HD29 | DNA sequence only |
| Cry1Cb2 | AAG35409 | Song et al | 2000 | Bt c001 | |
| Cry1Cb3 | ACD50894 | Huang et al | 2008 | Bt 087 | |
| Cry1Cb-like | AAX63901 | Thammasittirong et al | 2005 | Bt TA476-1 | insufficient sequence |
| Cry1Da1 | CAA38099 | Hofte et al | 1990 | Bt aizawai HD68 | |
| Cry1Da2 | I76415 | Payne & Sick | 1997 | | DNA sequence only |
| Cry1Db1 | CAA80234 | Lambert | 1993 | Bt BTS00349A | |
| Cry1Db2 | AAK48937 | Li et al | 2001 | Bt B-Pr-88 | |
| Cry1Dc1 | ABK35074 | Lertwiriyawong et al | 2006 | Bt JC291 | |
| Cry1Ea1 | CAA37933 | Visser et al | 1990 | Bt kenyae 4F1 | |
| Cry1Ea2 | CAA39609 | Bosse et al | 1990 | Bt kenyae | |
| Cry1Ea3 | AAA22345 | Feitelson | 1991 | Bt kenyae PS81F | |
| Cry1Ea4 | AAD04732 | Barboza-Corona et al | 1998 | Bt kenyae LBIT-147 | |
| Cry1Ea5 | A15535 | Botterman et al | 1994 | | DNA sequence only |
| Cry1Ea6 | AAL50330 | Sun et al | 1999 | Bt YBT-032 | |
| Cry1Ea7 | AAW72936 | Huehne et al | 2005 | Bt JC190 | |
| Cry1Ea8 | ABX11258 | Huang et al | 2007 | Bt HZM2 | |

APPENDIX A-continued

List of delta-endotoxins - from Crickmore et al. website (cited in application)
Accession Number is to NCBI entry (if available)

| | | | | | |
|---|---|---|---|---|---|
| Cry1Eb1 | AAA22346 | Feitelson | 1993 | Bt aizawai PS81A2 | |
| Cry1Fa1 | AAA22348 | Chambers et al | 1991 | Bt aizawai EG6346 | |
| Cry1Fa2 | AAA22347 | Feitelson | 1993 | Bt aizawai PS81I | |
| Cry1Fb1 | CAA80235 | Lambert | 1993 | Bt BTS00349A | |
| Cry1Fb2 | BAA25298 | Masuda & Asano | 1998 | Bt morrisoni INA67 | |
| Cry1Fb3 | AAF21767 | Song et al | 1998 | Bt morrisoni | |
| Cry1Fb4 | AAC10641 | Payne et al | 1997 | | |
| Cry1Fb5 | AAO13295 | Li et al | 2001 | Bt B-Pr-88 | |
| Cry1Fb6 | ACD50892 | Huang et al | 2008 | Bt 012 | |
| Cry1Fb7 | ACD50893 | Huang et al | 2008 | Bt 087 | |
| Cry1Ga1 | CAA80233 | Lambert | 1993 | Bt BTS0349A | |
| Cry1Ga2 | CAA70506 | Shevelev et al | 1997 | Bt wuhanensis | |
| Cry1Gb1 | AAD10291 | Kuo & Chak | 1999 | Bt wuhanensis HD525 | |
| Cry1Gb2 | AAO13756 | Li et al | 2000 | Bt B-Pr-88 | |
| Cry1Gc | AAQ52381 | Baum et al | 2003 | | |
| Cry1Ha1 | CAA80236 | Lambert | 1993 | Bt BTS02069AA | |
| Cry1Hb1 | AAA79694 | Koo et al | 1995 | Bt morrisoni BF190 | |
| Cry1H-like | AAF01213 | Srifah et al | 1999 | Bt JC291 | insufficient sequence |
| Cry1Ia1 | CAA44633 | Tailor et al | 1992 | Bt kurstaki | |
| Cry1Ia2 | AAA22354 | Gleave et al | 1993 | Bt kurstaki | |
| Cry1Ia3 | AAC36999 | Shin et al | 1995 | Bt kurstaki HD1 | |
| Cry1Ia4 | AAB00958 | Kostichka et al | 1996 | Bt AB88 | |
| Cry1Ia5 | CAA70124 | Selvapandiyan | 1996 | Bt 61 | |
| Cry1Ia6 | AAC26910 | Zhong et al | 1998 | Bt kurstaki S101 | |
| Cry1Ia7 | AAM73516 | Porcar et al | 2000 | Bt | |
| Cry1Ia8 | AAK66742 | Song et al | 2001 | | |
| Cry1Ia9 | AAQ08616 | Yao et al | 2002 | Bt Ly30 | |
| Cry1Ia10 | AAP86782 | Espindola et al | 2003 | Bt thuringiensis | |
| Cry1Ia11 | CAC85964 | Tounsi et al | 2003 | Bt kurstaki BNS3 | |
| Cry1Ia12 | AAV53390 | Grossi de Sa et al | 2005 | Bt | |
| Cry1Ia13 | ABF83202 | Martins et al | 2006 | Bt | |
| Cry1Ia14 | ACG63871 | Liu & Guo | 2008 | Bt11 | |
| Cry1Ia15 | FJ617445 | Guan Peng et al | 2009 | Bt E-1B | No NCBI link July 2009 |
| Cry1Ia16 | FJ617448 | Guan Peng et al | 2009 | Bt E-1A | No NCBI link July 2009 |
| Cry1Ib1 | AAA82114 | Shin et al | 1995 | Bt entomocidus BP465 | |
| Cry1Ib2 | ABW88019 | Guan et al | 2007 | Bt PP61 | |
| Cry1Ib3 | ACD75515 | Liu & Guo | 2008 | Bt GS8 | |
| Cry1Ic1 | AAC62933 | Osman et al | 1998 | Bt C18 | |
| Cry1Ic2 | AAE71691 | Osman et al | 2001 | | |
| Cry1Id1 | AAD44366 | Choi | 2000 | | |
| Cry1Ie1 | AAG43526 | Song et al | 2000 | Bt BTC007 | |
| Cry1If1 | AAQ52382 | Baum et al | 2003 | | |
| Cry1I-like | AAC31094 | Payne et al | 1998 | | insufficient sequence |
| Cry1I-like | ABG88859 | Lin & Fang | 2006 | Bt ly4a3 | insufficient sequence |
| Cry1Ja1 | AAA22341 | Donovan | 1994 | Bt EG5847 | |
| Cry1Jb1 | AAA98959 | Von Tersch & Gonzalez | 1994 | Bt EG5092 | |
| Cry1Jc1 | AAC31092 | Payne et al | 1998 | | |
| Cry1Jc2 | AAQ52372 | Baum et al | 2003 | | |
| Cry1Jd1 | CAC50779 | Arnaut et al | 2001 | Bt | |
| Cry1Ka1 | AAB00376 | Koo et al | 1995 | Bt morrisoni BF190 | |
| Cry1La1 | AAS60191 | Je et al | 2004 | Bt kurstaki K1 | |
| Cry1-like | AAC31091 | Payne et al | 1998 | | insufficient sequence |
| Cry2Aa1 | AAA22335 | Donovan et al | 1989 | Bt kurstaki | |
| Cry2Aa2 | AAA83516 | Widner & Whiteley | 1989 | Bt kurstaki HD1 | |
| Cry2Aa3 | D86064 | Sasaki et al | 1997 | Bt sotto | DNA sequence only |
| Cry2Aa4 | AAC04867 | Misra et al | 1998 | Bt kenyae HD549 | |
| Cry2Aa5 | CAA10671 | Yu & Pang | 1999 | Bt SL39 | |
| Cry2Aa6 | CAA10672 | Yu & Pang | 1999 | Bt YZ71 | |
| Cry2Aa7 | CAA10670 | Yu & Pang | 1999 | Bt CY29 | |
| Cry2Aa8 | AAO13734 | Wei et al | 2000 | Bt Dongbei 66 | |
| Cry2Aa9 | AAO13750 | Zhang et al | 2000 | | |
| Cry2Aa10 | AAQ04263 | Yao et al | 2001 | | |
| Cry2Aa11 | AAQ52384 | Baum et al | 2003 | | |
| Cry2Aa12 | ABI83671 | Tan et al | 2006 | Bt Rpp39 | |
| Cry2Aa13 | ABL01536 | Arango et al | 2008 | Bt 146-158-01 | |
| Cry2Aa14 | ACF04939 | Hire et al | 2008 | Bt HD-550 | |

APPENDIX A-continued

List of delta-endotoxins - from Crickmore et al. website (cited in application)
Accession Number is to NCBI entry (if available)

| | | | | | |
|---|---|---|---|---|---|
| Cry2Ab1 | AAA22342 | Widner & Whiteley | 1989 | Bt kurstaki HD1 | |
| Cry2Ab2 | CAA39075 | Dankocsik et al | 1990 | Bt kurstaki HD1 | |
| Cry2Ab3 | AAG36762 | Chen et al | 1999 | Bt BTC002 | |
| Cry2Ab4 | AAO13296 | Li et al | 2001 | Bt B-Pr-88 | |
| Cry2Ab5 | AAQ04609 | Yao et al | 2001 | Bt ly30 | |
| Cry2Ab6 | AAP59457 | Wang et al | 2003 | Bt WZ-7 | |
| Cry2Ab7 | AAZ66347 | Udayasuriyan et al | 2005 | Bt 14-1 | |
| Cry2Ab8 | ABC95996 | Huang et al | 2006 | Bt WB2 | |
| Cry2Ab9 | ABC74968 | Zhang et al | 2005 | Bt LLB6 | |
| Cry2Ab10 | EF157306 | Lin et al | 2006 | Bt LyD | |
| Cry2Ab11 | CAM84575 | Saleem et al | 2007 | Bt CMBL-BT1 | |
| Cry2Ab12 | ABM21764 | Lin et al | 2007 | Bt LyD | |
| Cry2Ab13 | ACG76120 | Zhu et al | 2008 | Bt ywc5-4 | |
| Cry2Ab14 | ACG76121 | Zhu et al | 2008 | Bt Bts | |
| Cry2Ac1 | CAA40536 | Aronson | 1991 | Bt shanghai S1 | |
| Cry2Ac2 | AAG35410 | Song et al | 2000 | | |
| Cry2Ac3 | AAQ52385 | Baum et al | 2003 | | |
| Cry2Ac4 | ABC95997 | Huang et al | 2006 | Bt WB9 | |
| Cry2Ac5 | ABC74969 | Zhang et al | 2005 | | |
| Cry2Ac6 | ABC74793 | Xia et al | 2006 | Bt wuhanensis | |
| Cry2Ac7 | CAL18690 | Saleem et al | 2008 | Bt SBSBT-1 | |
| Cry2Ac8 | CAM09325 | Saleem et al | 2007 | Bt CMBL-BT1 | |
| Cry2Ac9 | CAM09326 | Saleem et al | 2007 | Bt CMBL-BT2 | |
| Cry2Ac10 | ABN15104 | Bai et al | 2007 | Bt QCL-1 | |
| Cry2Ac11 | CAM83895 | Saleem et al | 2007 | Bt HD29 | |
| Cry2Ac12 | CAM83896 | Saleem et al | 2007 | Bt CMBL-BT3 | |
| Cry2Ad1 | AAF09583 | Choi et al | 1999 | Bt BR30 | |
| Cry2Ad2 | ABC86927 | Huang et al | 2006 | Bt WB10 | |
| Cry2Ad3 | CAK29504 | Saleem et al | 2006 | Bt 5_2AcT(1) | |
| Cry2Ad4 | CAM32331 | Saleem et al | 2007 | Bt CMBL-BT2 | |
| Cry2Ad5 | CAO78739 | Saleem et al | 2007 | Bt HD29 | |
| Cry2Ae1 | AAQ52362 | Baum et al | 2003 | | |
| Cry2Af1 | ABO30519 | Beard et al | 2007 | Bt C81 | |
| Cry2Ag | ACH91610 | Zhu et al | 2008 | Bt JF19-2 | |
| Cry2Ah | EU939453 | Zhang et al | 2008 | Bt | No NCBI link July 09 |
| Cry2Ah2 | ACL80665 | Zhang et al | 2009 | Bt BRC-ZQL3 | |
| Cry2Ai | FJ788388 | Udayasuriyan et al | 2009 | Bt | No NCBI link July 09 |
| Cry3Aa1 | AAA22336 | Herrnstadt et al | 1987 | Bt san diego | |
| Cry3Aa2 | AAA22541 | Sekar et al | 1987 | Bt tenebrionis | |
| Cry3Aa3 | CAA68482 | Hofte et al | 1987 | | |
| Cry3Aa4 | AAA22542 | McPherson et al | 1988 | Bt tenebrionis | |
| Cry3Aa5 | AAA50255 | Donovan et al | 1988 | Bt morrisoni EG2158 | |
| Cry3Aa6 | AAC43266 | Adams et al | 1994 | Bt tenebrionis | |
| Cry3Aa7 | CAB41411 | Zhang et al | 1999 | Bt 22 | |
| Cry3Aa8 | AAS79487 | Gao and Cai | 2004 | Bt YM-03 | |
| Cry3Aa9 | AAW05659 | Bulla and Candas | 2004 | Bt UTD-001 | |
| Cry3Aa10 | AAU29411 | Chen et al | 2004 | Bt 886 | |
| Cry3Aa11 | AAW82872 | Kurt et al | 2005 | Bt tenebrionis Mm2 | |
| Cry3Aa12 | ABY49136 | Sezen et al | 2008 | Bt tenebrionis | |
| Cry3Ba1 | CAA34983 | Sick et al | 1990 | Bt tolworthi 43F | |
| Cry3Ba2 | CAA00645 | Peferoen et al | 1990 | Bt PGSI208 | |
| Cry3Bb1 | AAA22334 | Donovan et al | 1992 | Bt EG4961 | |
| Cry3Bb2 | AAA74198 | Donovan et al | 1995 | Bt EG5144 | |
| Cry3Bb3 | I15475 | Peferoen et al | 1995 | | DNA sequence only |
| Cry3Ca1 | CAA42469 | Lambert et al | 1992 | Bt kurstaki BtI109P | |
| Cry4Aa1 | CAA68485 | Ward & Ellar | 1987 | Bt israelensis | |
| Cry4Aa2 | BAA00179 | Sen et al | 1988 | Bt israelensis HD522 | |
| Cry4Aa3 | CAD30148 | Berry et al | 2002 | Bt israelensis | |
| Cry4A-like | AAY96321 | Mahalakshmi et al | 2005 | Bt LDC-9 | insufficient sequence |
| Cry4Ba1 | CAA30312 | Chungjatpornchai et al | 1988 | Bt israelensis 4Q2-72 | |
| Cry4Ba2 | CAA30114 | Tungpradubkul et al | 1988 | Bt israelensis | |
| Cry4Ba3 | AAA22337 | Yamamoto et al | 1988 | Bt israelensis | |
| Cry4Ba4 | BAA00178 | Sen et al | 1988 | Bt israelensis HD522 | |
| Cry4Ba5 | CAD30095 | Berry et al | 2002 | Bt israelensis | |
| Cry4Ba-like | ABC47686 | Mahalakshmi et al | 2005 | Bt LDC-9 | insufficient sequence |
| Cry4Ca1 | EU646202 | Shu et al | 2008 | | No NCBI link July 09 |
| Cry4Cb1 | FJ403208 | Jun & Furong | 2008 | Bt HS18-1 | No NCBI link July 09 |
| Cry4Cb2 | FJ597622 | Jun & Furong | 2008 | Bt Ywc2-8 | No NCBI link July 09 |
| Cry4Cc1 | FJ403207 | Jun & Furong | 2008 | Bt MC28 | No NCBI link July 09 |

APPENDIX A-continued

List of delta-endotoxins - from Crickmore et al. website (cited in application)
Accession Number is to NCBI entry (if available)

| | | | | | |
|---|---|---|---|---|---|
| Cry5Aa1 | AAA67694 | Narva et al | 1994 | Bt darmstadiensis PS17 | |
| Cry5Ab1 | AAA67693 | Narva et al | 1991 | Bt darmstadiensis PS17 | |
| Cry5Ac1 | I34543 | Payne et al | 1997 | | DNA sequence only |
| Cry5Ad1 | ABQ82087 | Lenane et al | 2007 | Bt L366 | |
| Cry5Ba1 | AAA68598 | Foncerrada & Narva | 1997 | Bt PS86Q3 | |
| Cry5Ba2 | ABW88932 | Guo et al | 2008 | YBT 1518 | |
| Cry6Aa1 | AAA22357 | Narva et al | 1993 | Bt PS52A1 | |
| Cry6Aa2 | AAM46849 | Bai et al | 2001 | YBT 1518 | |
| Cry6Aa3 | ABH03377 | Jia et al | 2006 | Bt 96418 | |
| Cry6Ba1 | AAA22358 | Narva et al | 1991 | Bt PS69D1 | |
| Cry7Aa1 | AAA22351 | Lambert et al | 1992 | Bt galleriae PGSI245 | |
| Cry7Ab1 | AAA21120 | Narva & Fu | 1994 | Bt dakota HD511 | |
| Cry7Ab2 | AAA21121 | Narva & Fu | 1994 | Bt kumamotoensis 867 | |
| Cry7Ab3 | ABX24522 | Song et al | 2008 | Bt WZ-9 | |
| Cry7Ab4 | EU380678 | Shu et al | 2008 | Bt | No NCBI link July 09 |
| Cry7Ab5 | ABX79555 | Aguirre-Arzola et al | 2008 | Bt monterrey GM-33 | |
| Cry7Ab6 | ACI44005 | Deng et al | 2008 | Bt HQ122 | |
| Cry7Ab7 | FJ940776 | Wang et al | 2009 | | No NCBI link Sept 09 |
| Cry7Ab8 | GU145299 | Feng Jing | 2009 | | No NCBI link Nov 09 |
| Cry7Ba1 | ABB70817 | Zhang et al | 2006 | Bt huazhongensis | |
| Cry7Ca1 | ABR67863 | Gao et al | 2007 | Bt BTH-13 | |
| Cry7Da1 | ACQ99547 | Yi et al | 2009 | Bt LH-2 | |
| Cry8Aa1 | AAA21117 | Narva & Fu | 1992 | Bt kumamotoensis | |
| Cry8Ab1 | EU044830 | Cheng et al | 2007 | Bt B-JJX | No NCBI link July 09 |
| Cry8Ba1 | AAA21118 | Narva & Fu | 1993 | Bt kumamotoensis | |
| Cry8Bb1 | CAD57542 | Abad et al | 2002 | | |
| Cry8Bc1 | CAD57543 | Abad et al | 2002 | | |
| Cry8Ca1 | AAA21119 | Sato et al. | 1995 | Bt japonensis Buibui | |
| Cry8Ca2 | AAR98783 | Shu et al | 2004 | Bt HBF-1 | |
| Cry8Ca3 | EU625349 | Du et al | 2008 | Bt FTL-23 | No NCBI link July 09 |
| Cry8Da1 | BAC07226 | Asano et al | 2002 | Bt galleriae | |
| Cry8Da2 | BD133574 | Asano et al | 2002 | Bt | DNA sequence only |
| Cry8Da3 | BD133575 | Asano et al | 2002 | Bt | DNA sequence only |
| Cry8Db1 | BAF93483 | Yamaguchi et al | 2007 | Bt BBT2-5 | |
| Cry8Ea1 | AAQ73470 | Fuping et al | 2003 | Bt 185 | |
| Cry8Ea2 | EU047597 | Liu et al | 2007 | Bt B-DLL | No NCBI link July 09 |
| Cry8Fa1 | AAT48690 | Shu et al | 2004 | Bt 185 | also AAW81032 |
| Cry8Ga1 | AAT46073 | Shu et al | 2004 | Bt HBF-18 | |
| Cry8Ga2 | ABC42043 | Yan et al | 2008 | Bt 145 | |
| Cry8Ga3 | FJ198072 | Xiaodong et al | 2008 | Bt FCD114 | No NCBI link July 09 |
| Cry8Ha1 | EF465532 | Fuping et al | 2006 | Bt 185 | No NCBI link July 09 |
| Cry8Ia1 | EU381044 | Yan et al | 2008 | Bt su4 | No NCBI link July 09 |
| Cry8Ja1 | EU625348 | Du et al | 2008 | Bt FPT-2 | No NCBI link July 09 |
| Cry8Ka1 | FJ422558 | Quezado et al | 2008 | | No NCBI link July 09 |
| Cry8Ka2 | ACN87262 | Noguera & Ibarra | 2009 | Bt kenyae | |
| Cry8-like | FJ770571 | Noguera & Ibarra | 2009 | Bt canadensis | DNA sequence only |
| Cry8-like | ABS53003 | Mangena et al | 2007 | Bt | |
| Cry9Aa1 | CAA41122 | Shevelev et al | 1991 | Bt galleriae | |
| Cry9Aa2 | CAA41425 | Gleave et al | 1992 | Bt DSIR517 | |
| Cry9Aa3 | GQ249293 | Su et al | 2009 | Bt SC5(D2) | No NCBI link July 09 |
| Cry9Aa4 | GQ249294 | Su et al | 2009 | Bt T03C001 | No NCBI link July 09 |
| Cry9Aa like | AAQ52376 | Baum et al | 2003 | | incomplete sequence |
| Cry9Ba1 | CAA52927 | Shevelev et al | 1993 | Bt galleriae | |
| Cry9Bb1 | AAV28716 | Silva-Werneck et al | 2004 | Bt japonensis | |
| Cry9Ca1 | CAA85764 | Lambert et al | 1996 | Bt tolworthi | |
| Cry9Ca2 | AAQ52375 | Baum et al | 2003 | | |
| Cry9Da1 | BAA19948 | Asano | 1997 | Bt japonensis N141 | |
| Cry9Da2 | AAB97923 | Wasano & Ohba | 1998 | Bt japonensis | |
| Cry9Da3 | GQ249295 | Su et al | 2009 | Bt T03B001 | No NCBI link July 09 |
| Cry9Da4 | GQ249297 | Su et al | 2009 | Bt T03B001 | No NCBI link July 09 |
| Cry9Db1 | AAX78439 | Flannagan & Abad | 2005 | Bt kurstaki DP1019 | |
| Cry9Ea1 | BAA34908 | Midoh & Oyama | 1998 | Bt aizawai SSK-10 | |
| Cry9Ea2 | AAO12908 | Li et al | 2001 | Bt B-Hm-16 | |
| Cry9Ea3 | ABM21765 | Lin et al | 2006 | Bt lyA | |
| Cry9Ea4 | ACE88267 | Zhu et al | 2008 | Bt ywc5-4 | |
| Cry9Ea5 | ACF04743 | Zhu et al | 2008 | Bts | |
| Cry9Ea6 | ACG63872 | Liu & Guo | 2008 | Bt 11 | |

APPENDIX A-continued

List of delta-endotoxins - from Crickmore et al. website (cited in application)
Accession Number is to NCBI entry (if available)

| | | | | | |
|---|---|---|---|---|---|
| Cry9Ea7 | FJ380927 | Sun et al | 2008 | | No NCBI link July 09 |
| Cry9Ea8 | GQ249292 | Su et al | 2009 | GQ249292 | No NCBI link July 09 |
| Cry9Eb1 | CAC50780 | Arnaut et al | 2001 | | |
| Cry9Eb2 | GQ249298 | Su et al | 2009 | Bt T03B001 | No NCBI link July 09 |
| Cry9Ec1 | AAC63366 | Wasano et al | 2003 | Bt galleriae | |
| Cry9Ed1 | AAX78440 | Flannagan & Abad | 2005 | Bt kurstaki DP1019 | |
| Cry9Ee1 | GQ249296 | Su et al | 2009 | Bt T03B001 | No NCBI link Aug 09 |
| Cry9-like | AAC63366 | Wasano et al | 1998 | Bt galleriae | insufficient sequence |
| Cry10Aa1 | AAA22614 | Thorne et al | 1986 | Bt israelensis | |
| Cry10Aa2 | E00614 | Aran & Toomasu | 1996 | Bt israelensis ONR-60A | DNA sequence only |
| Cry10Aa3 | CAD30098 | Berry et al | 2002 | Bt israelensis | |
| Cry10A-like | DQ167578 | Mahalakshmi et al | 2006 | Bt LDC-9 | incomplete sequence |
| Cry11Aa1 | AAA22352 | Donovan et al | 1988 | Bt israelensis | |
| Cry11Aa2 | AAA22611 | Adams et al | 1989 | Bt israelensis | |
| Cry11Aa3 | CAD30081 | Berry et al | 2002 | Bt israelensis | |
| Cry11Aa-like | DQ166531 | Mahalakshmi et al | 2007 | Bt LDC-9 | incomplete sequence |
| Cry11Ba1 | CAA60504 | Delecluse et al | 1995 | Bt jegathesan 367 | |
| Cry11Bb1 | AAC97162 | Orduz et al | 1998 | Bt medellin | |
| Cry12Aa1 | AAA22355 | Narva et al | 1991 | Bt PS33F2 | |
| Cry13Aa1 | AAA22356 | Narva et al | 1992 | Bt PS63B | |
| Cry14Aa1 | AAA21516 | Narva et al | 1994 | Bt sotto PS80JJ1 | |
| Cry15Aa1 | AAA22333 | Brown & Whiteley | 1992 | Bt thompsoni | |
| Cry16Aa1 | CAA63860 | Barloy et al | 1996 | Cb malaysia CH18 | |
| Cry17Aa1 | CAA67841 | Barloy et al | 1998 | Cb malaysia CH18 | |
| Cry18Aa1 | CAA67506 | Zhang et al | 1997 | Paenibacillus popilliae | |
| Cry18Ba1 | AAF89667 | Patel et al | 1999 | Paenibacillus popilliae | |
| Cry18Ca1 | AAF89668 | Patel et al | 1999 | Paenibacillus popilliae | |
| Cry19Aa1 | CAA68875 | Rosso & Delecluse | 1996 | Bt jegathesan 367 | |
| Cry19Ba1 | BAA32397 | Hwang et al | 1998 | Bt higo | |
| Cry20Aa1 | AAB93476 | Lee & Gill | 1997 | Bt fukuokaensis | |
| Cry20Ba1 | ACS93601 | Noguera & Ibarra | 2009 | Bt higo LBIT-976 | |
| Cry20-like | GQ144333 | Yi et al | 2009 | Bt Y-5 | DNA sequence only |
| Cry21Aa1 | I32932 | Payne et al | 1996 | | DNA sequence only |
| Cry21Aa2 | I66477 | Feitelson | 1997 | | DNA sequence only |
| Cry21Ba1 | BAC06484 | Sato & Asano | 2002 | Bt roskildiensis | |
| Cry22Aa1 | I34547 | Payne et al | 1997 | | DNA sequence only |
| Cry22Aa2 | CAD43579 | Isaac et al | 2002 | Bt | |
| Cry22Aa3 | ACD93211 | Du et al | 2008 | Bt FZ-4 | |
| Cry22Ab1 | AAK50456 | Baum et al | 2000 | Bt EG4140 | |
| Cry22Ab2 | CAD43577 | Isaac et al | 2002 | Bt | |
| Cry22Ba1 | CAD43578 | Isaac et al | 2002 | Bt | |
| Cry23Aa1 | AAF76375 | Donovan et al | 2000 | Bt | Binary with Cry37Aa1 |
| Cry24Aa1 | AAC61891 | Kawalek and Gill | 1998 | Bt jegathesan | |
| Cry24Ba1 | BAD32657 | Ohgushi et al | 2004 | Bt sotto | |
| Cry24Ca1 | CAJ43600 | Beron & Salerno | 2005 | Bt FCC-41 | |
| Cry25Aa1 | AAC61892 | Kawalek and Gill | 1998 | Bt jegathesan | |
| Cry26Aa1 | AAD25075 | Wojciechowska et al | 1999 | Bt finitimus B-1166 | |
| Cry27Aa1 | BAA82796 | Saitoh | 1999 | Bt higo | |
| Cry28Aa1 | AAD24189 | Wojciechowska et al | 1999 | Bt finitimus B-1161 | |
| Cry28Aa2 | AAG00235 | Moore and Debro | 2000 | Bt finitimus | |
| Cry29Aa1 | CAC80985 | Delecluse et al | 2000 | Bt medellin | |
| Cry30Aa1 | CAC80986 | Delecluse et al | 2000 | Bt medellin | |
| Cry30Ba1 | BAD00052 | Ito et al | 2003 | Bt entomocidus | |
| Cry30Ca1 | BAD67157 | Ohgushi et al | 2004 | Bt sotto | |
| Cry30Ca2 | ACU24781 | Sun and Park | 2009 | Bt jegathesan 367 | |
| Cry30Da1 | EF095955 | Shu et al | 2006 | Bt Y41 | No NCBI link July09 |
| Cry30Db1 | BAE80088 | Kishida et al | 2006 | Bt aizawai BUN1-14 | |
| Cry30Ea1 | ACC95445 | Fang et al | 2007 | Bt S2160-1 | |
| Cry30Ea2 | FJ499389 | Jun et al | 2008 | Bt Ywc2-8 | No NCBI link July09 |
| Cry30Fa1 | ACI22625 | Tan et al | 2008 | Bt MC28 | |
| Cry30Ga1 | ACG60020 | Zhu et al | 2008 | Bt HS18-1 | |
| Cry31Aa1 | BAB11757 | Saitoh & Mizuki | 2000 | Bt 84-HS-1-11 | |
| Cry31Aa2 | AAL87458 | Jung and Cote | 2000 | Bt M15 | |
| Cry31Aa3 | BAE79808 | Uemori et al | 2006 | Bt B0195 | |
| Cry31Aa4 | BAF32571 | Yasutake et al | 2006 | Bt 79-25 | |
| Cry31Aa5 | BAF32572 | Yasutake et al | 2006 | Bt 92-10 | |
| Cry31Ab1 | BAE79809 | Uemori et al | 2006 | Bt B0195 | |

APPENDIX A-continued

List of delta-endotoxins - from Crickmore et al. website (cited in application)
Accession Number is to NCBI entry (if available)

| | | | | | |
|---|---|---|---|---|---|
| Cry31Ab2 | BAF32570 | Yasutake et al | 2006 | Bt 31-5 | |
| Cry31Ac1 | BAF34368 | Yasutake et al | 2006 | Bt 87-29 | |
| Cry32Aa1 | AAG36711 | Balasubramanian et al | 2001 | Bt yunnanensis | |
| Cry32Ba1 | BAB78601 | Takebe et al | 2001 | Bt | |
| Cry32Ca1 | BAB78602 | Takebe et al | 2001 | Bt | |
| Cry32Da1 | BAB78603 | Takebe et al | 2001 | Bt | |
| Cry33Aa1 | AAL26871 | Kim et al | 2001 | Bt dakota | |
| Cry34Aa1 | AAG50341 | Ellis et al | 2001 | Bt PS80JJ1 | Binary with Cry35Aa1 |
| Cry34Aa2 | AAK64560 | Rupar et al | 2001 | Bt EG5899 | Binary with Cry35Aa2 |
| Cry34Aa3 | AAT29032 | Schnepf et al | 2004 | Bt PS69Q | Binary with Cry35Aa3 |
| Cry34Aa4 | AAT29030 | Schnepf et al | 2004 | Bt PS185GG | Binary with Cry35Aa4 |
| Cry34Ab1 | AAG41671 | Moellenbeck et al | 2001 | Bt PS149B1 | Binary with Cry35Ab1 |
| Cry34Ac1 | AAG50118 | Ellis et al | 2001 | Bt PS167H2 | Binary with Cry35Ac1 |
| Cry34Ac2 | AAK64562 | Rupar et al | 2001 | Bt EG9444 | Binary with Cry35Ab2 |
| Cry34Ac3 | AAT29029 | Schnepf et al | 2004 | Bt KR1369 | Binary with Cry35Ab3 |
| Cry34Ba1 | AAK64565 | Rupar et al | 2001 | Bt EG4851 | Binary with Cry35Ba1 |
| Cry34Ba2 | AAT29033 | Schnepf et al | 2004 | Bt PS201L3 | Binary with Cry35Ba2 |
| Cry34Ba3 | AAT29031 | Schnepf et al | 2004 | Bt PS201HH2 | Binary with Cry35Ba3 |
| Cry35Aa1 | AAG50342 | Ellis et al | 2001 | Bt PS80111 | Binary with Cry34Aa1 |
| Cry35Aa2 | AAK64561 | Rupar et al | 2001 | Bt EG5899 | Binary with Cry34Aa2 |
| Cry35Aa3 | AAT29028 | Schnepf et al | 2004 | Bt PS69Q | Binary with Cry34Aa3 |
| Cry35Aa4 | AAT29025 | Schnepf et al | 2004 | Bt PS185GG | Binary with Cry34Aa4 |
| Cry35Ab1 | AAG41672 | Moellenbeck et al | 2001 | Bt PS149B1 | Binary with Cry34Ab1 |
| Cry35Ab2 | AAK64563 | Rupar et al | 2001 | Bt EG9444 | Binary with Cry34Ac2 |
| Cry35Ab3 | AY536891 | AAT29024 | 2004 | Bt KR1369 | Binary with Cry34Ab3 |
| Cry35Ac1 | AAG50117 | Ellis et al | 2001 | Bt PS167H2 | Binary with Cry34Ac1 |
| Cry35Ba1 | AAK64566 | Rupar et al | 2001 | Bt EG4851 | Binary with Cry34Ba1 |
| Cry35Ba2 | AAT29027 | Schnepf et al | 2004 | Bt PS201L3 | Binary with Cry34Ba2 |
| Cry35Ba3 | AAT29026 | Schnepf et al | 2004 | Bt PS201HH2 | Binary with Cry34Ba3 |
| Cry36Aa1 | AAK64558 | Rupar et al | 2001 | Bt | |
| Cry37Aa1 | AAF76376 | Donovan et al | 2000 | Bt | Binary with Cry23Aa |
| Cry38Aa1 | AAK64559 | Rupar et al | 2000 | Bt | |
| Cry39Aa1 | BAB72016 | Ito et al | 2001 | Bt aizawai | |
| Cry40Aa1 | BAB72018 | Ito et al | 2001 | Bt aizawai | |
| Cry40Ba1 | BAC77648 | Ito et al | 2003 | Bun1-14 | |
| Cry40Ca1 | EU381045 | Shu et al | 2008 | Bt Y41 | No NCBI link July09 |
| Cry40Da1 | ACF15199 | Zhang et al | 2008 | Bt S2096-2 | |
| Cry41Aa1 | BAD35157 | Yamashita et al | 2003 | Bt A1462 | |
| Cry41Ab1 | BAD35163 | Yamashita et al | 2003 | Bt A1462 | |
| Cry42Aa1 | BAD35166 | Yamashita et al | 2003 | Bt A1462 | |
| Cry43Aa1 | BAD15301 | Yokoyama and Tanaka | 2003 | P. lentimorbus semadara | |
| Cry43Aa2 | BAD95474 | Nozawa | 2004 | P. popilliae popilliae | |
| Cry43Ba1 | BAD15303 | Yokoyama and Tanaka | 2003 | P. lentimorbus semadara | |
| Cry43-like | BAD15305 | Yokoyama and Tanaka | 2003 | P. lentimorbus semadara | |
| Cry44Aa | BAD08532 | Ito et al | 2004 | Bt entomocidus INA288 | |
| Cry45Aa | BAD22577 | Okumura et al | 2004 | Bt 89-T-34-22 | |
| Cry46Aa | BAC79010 | Ito et al | 2004 | Bt dakota | |
| Cry46Aa2 | BAG68906 | Ishikawa et al | 2008 | Bt A1470 | |
| Cry46Ab | BAD35170 | Yamagiwa et al | 2004 | Bt | |
| Cry47Aa | AAY24695 | Kongsuwan et al | 2005 | Bt CAA890 | |
| Cry48Aa | CAJ18351 | Jones and Berry | 2005 | Bs IAB59 | binary with 49Aa |
| Cry48Aa2 | CAJ86545 | Jones and Berry | 2006 | Bs 47-6B | binary with 49Aa2 |
| Cry48Aa3 | CAJ86546 | Jones and Berry | 2006 | Bs NHA15b | binary with 49Aa3 |
| Cry48Ab | CAJ86548 | Jones and Berry | 2006 | Bs LP1G | binary with 49Ab1 |
| Cry48Ab2 | CAJ86549 | Jones and Berry | 2006 | Bs 2173 | binary with 49Aa4 |
| Cry49Aa | CAH56541 | Jones and Berry | 2005 | Bs IAB59 | binary with 48Aa |
| Cry49Aa2 | CAJ86541 | Jones and Berry | 2006 | Bs 47-6B | binary with 48Aa2 |
| Cry49Aa3 | CAJ86543 | Jones and Berry | 2006 | BsNHA15b | binary with 48Aa3 |
| Cry49Aa4 | CAJ86544 | Jones and Berry | 2006 | Bs 2173 | binary with 48Ab2 |
| Cry49Ab1 | CAJ86542 | Jones and Berry | 2006 | Bs LP1G | binary with 48Ab1 |
| Cry50Aa1 | BAE86999 | Ohgushi et al | 2006 | Bt sotto | |
| Cry51Aa1 | ABI14444 | Meng et al | 2006 | Bt F14-1 | |
| Cry52Aa1 | EF613489 | Song et al | 2007 | Bt Y41 | No NCBI link July09 |
| Cry52Ba1 | FJ361760 | Jun et al | 2008 | Bt BM59-2 | No NCBI link July09 |
| Cry53Aa1 | EF633476 | Song et al | 2007 | Bt Y41 | No NCBI link July09 |
| Cry53Ab1 | FJ361759 | Jun et al | 2008 | Bt MC28 | No NCBI link July09 |
| Cry54Aa1 | ACA52194 | Tan et al | 2009 | Bt MC28 | |
| Cry55Aa1 | ABW88931 | Guo et al | 2008 | YBT 1518 | |
| Cry55Aa2 | AAE33526 | Bradfisch et al | 2000 | BT Y41 | |
| Cry56Aa1 | FJ597621 | Jun & Furong | 2008 | Bt Ywc2-8 | No NCBI link July09 |
| Cry56Aa2 | GQ483512 | Guan Peng et al | 2009 | Bt G7-1 | No NCBI link Aug09 |

APPENDIX A-continued

List of delta-endotoxins - from Crickmore et al. website (cited in application)
Accession Number is to NCBI entry (if available)

| | | | | |
|---|---|---|---|---|
| Cry57Aa1 | ANC87261 | Noguera & Ibarra | 2009 | Bt kim |
| Cry58Aa1 | ANC87260 | Noguera & Ibarra | 2009 | Bt entomocidus |
| Cry59Aa1 | ACR43758 | Noguera & Ibarra | 2009 | Bt kim LBIT-980 |

| | | | | | | | |
|---|---|---|---|---|---|---|---|
| Vip3Aa1 | Vip3Aa | AAC37036 | Estruch et al | 1996 | PNAS 93, 5389-5394 | AB88 | |
| Vip3Aa2 | Vip3Ab | AAC37037 | Estruch et al | 1996 | PNAS 93, 5389-5394 | AB424 | |
| Vip3Aa3 | Vip3Ac | | Estruch et al | 2000 | U.S. Pat. No. 6,137,033 October 2000 | | |
| Vip3Aa4 | PS36A Sup | AAR81079 | Feitelson et al | 1998 | U.S. Pat. No. 6,656,908 December 2003 | Bt PS36A | WO9818932(A2, A3) 7 May 1998 |
| Vip3Aa5 | PS81F Sup | AAR81080 | Feitelson et al | 1998 | U.S. Pat. No. 6,656,908 December 2003 | Bt PS81F | WO9818932(A2, A3) 7 May 1998 |
| Vip3Aa6 | Jav90 Sup | AAR81081 | Feitelson et al | 1998 | U.S. Pat. No. 6,656,908 December 2003 | Bt | WO9818932(A2, A3) 7 May 1998 |
| Vip3Aa7 | Vip83 | AAK95326 | Cai et al | 2001 | unpublished | Bt YBT-833 | |
| Vip3Aa8 | Vip3A | AAK97481 | Loguercio et al | 2001 | unpublished | Bt HD125 | |
| Vip3Aa9 | VipS | CAA76665 | Selvapandiyan et al | 2001 | unpublished | Bt A13 | |
| Vip3Aa10 | Vip3V | AAN60738 | Doss et al | 2002 | Protein Expr. Purif. 26, 82-88 | Bt | |
| Vip3Aa11 | Vip3A | AAR36859 | Liu et al | 2003 | unpublished | Bt C9 | |
| Vip3Aa12 | Vip3A-WB5 | AAM22456 | Wu and Guan | 2003 | unpublished | Bt | |
| Vip3Aa13 | Vip3A | AAL69542 | Chen et al | 2002 | Sheng Wu Gong Cheng Xue Bao 18, 687-692 | Bt S184 | |
| Vip3Aa14 | Vip | AAQ12340 | Polumetla et al | 2003 | unpublished | Bt tolworthi | |
| Vip3Aa15 | Vip3A | AAP51131 | Wu et al | 2004 | unpublished | Bt WB50 | |
| Vip3Aa16 | Vip3LB | AAW65132 | Mesrati et al | 2005 | FEMS Micro Lett 244, 353-358 | Bt | |
| Vip3Aa17 | Jav90 | | Feitelson et al | 1999 | U.S. Pat. No. 6,603,063 August 2003 | Javelin 1990 | WO9957282(A2, A3) 11Nov 1999 |
| Vip3Aa18 | | AAX49395 | Cai and Xiao | 2005 | unpublished | Bt 9816C | |
| Vip3Aa19 | Vip3ALD | DQ241674 | Liu et al | 2006 | unpublished | Bt AL | |
| Vip3Aa19 | Vip3A-1 | DQ539887 | Hart et al | 2006 | unpublished | | |
| Vip3Aa20 | Vip3A-2 | DQ539888 | Hart et al | 2006 | unpublished | | |
| Vip3Aa21 | Vip | ABD84410 | Panbangred | 2006 | unpublished | Bt aizawai | |
| Vip3Aa22 | Vip3A-LS1 | AAY41427 | Lu et al | 2005 | unpublished | Bt LS1 | |
| Vip3Aa23 | Vip3A-LS8 | AAY41428 | Lu et al | 2005 | unpublished | Bt LS8 | |
| Vip3Aa24 | | BI 880913 | Song et al | 2007 | unpublished | Bt WZ-7 | |
| Vip3Aa25 | | EF608501 | Hsieh et al | 2007 | unpublished | | |
| Vip3Aa26 | | EU294496 | Shen and Guo | 2007 | unpublished | Bt TF9 | |
| Vip3Aa27 | | EU332167 | Shen and Guo | 2007 | unpublished | Bt 16 | |
| Vip3Aa28 | | FJ494817 | Xiumei Yu | 2008 | unpublished | Bt JF23-8 | |
| Vip3Aa29 | | FJ626674 | Xieumei et al | 2009 | unpublished | Bt JF21-1 | |
| Vip3Aa30 | | FJ626675 | Xieumei et al | 2009 | unpublished | MD2-1 | |
| Vip3Aa31 | | FJ626676 | Xieumei et al | 2009 | unpublished | JF21-1 | |
| Vip3Aa32 | | FJ626677 | Xieumei et al | 2009 | unpublished | MD2-1 | |
| — | | | | — | | | |
| Vip3Ab1 | Vip3B | AAR40284 | Feitelson et al | 1999 | U.S. Pat. No. 6,603,063 August 2003 | Bt KB59A4-6 | WO9957282(A2, A3) 11Nov 1999 |
| Vip3Ab2 | Vip3D | AAY88247 | Feng and Shen | 2006 | unpublished | Bt | |
| — | | | | — | | | |
| Vip3Ac1 | PS49C | | Narva et al | — | US application 20040128716 | | |
| — | | | | — | | | |
| Vip3Ad1 | PS158C2 | | Narva et al | — | US application 20040128716 | | |
| Vip3Ad2 | ISP3B | CAI43276 | Van Rie et al | 2005 | unpublished | Bt | |
| — | | | | — | | | |
| Vip3Ae1 | ISP3C | CAI43277 | Van Rie et al | 2005 | unpublished | Bt | |
| — | | | | — | | | |
| Vip3Af1 | ISP3A | CAI43275 | Van Rie et al | 2005 | unpublished | Bt | |
| Vip3Af2 | Vip3C | ADN08753 | Syngenta | — | WO 03/075655 | | |
| — | | | | — | | | |

APPENDIX A-continued

List of delta-endotoxins - from Crickmore et al. website (cited in application)
Accession Number is to NCBI entry (if available)

| | | | | | | |
|---|---|---|---|---|---|---|
| Vip3Ag1 | Vip3B | ADN08758 | Syngenta | — | WO 02/078437 | |
| Vip3Ag2 | | FJ556803 | Audtho et al | 2008 | | Bt |
| — | | | | — | | |
| Vip3Ah1 | Vip3S | DQ832323 | Li and Shen | 2006 | unpublished | Bt |
| — | | | | | | |
| Vip3Ba1 | | AAV70653 | Rang et al | 2004 | unpublished | |
| — | | | | | | |
| Vip3Bb1 | Vip3Z | ADN08760 | Syngenta | — | WO 03/075655 | |
| Vip3Bb2 | | EF439819 | Akhurst et al | 2007 | | |

We claim:

1. A transgenic plant comprising a DNA encoding the Cry1Ca insecticidal protein of SEQ ID NO:5 and a DNA encoding the Cry1Fa insecticidal protein of SEQ ID NO:4.

2. A seed of the plant of claim 1 wherein the seed comprises said DNA encoding said Cry1Ca insecticidal protein and said DNA encoding said Cry1Fa insecticidal protein.

3. A population of plants comprising non-Bt refuge plants and a plurality of the transgenic plants of claim 1, wherein said refuge plants comprise less than 40% of said population of plants.

4. The population of plants of claim 3, wherein said refuge plants comprise less than 5% of said population of plants.

5. A mixture of seeds comprising refuge seeds from non-Bt refuge plants, and a plurality of seeds of claim 2, wherein said refuge seeds comprise less than 40% of all the seeds in the mixture.

6. The mixture of seeds of claim 5, wherein said refuge seeds comprise less than 5% of all the seeds in the mixture.

7. The transgenic plant of claim 1, said plant further comprising DNA encoding a Cry1Ab core toxin-containing protein.

8. A of plants comprising non-Bt refuge plants and a plurality of transgenic plants of claim 7, wherein said refuge plants comprise less than about 20% of said population of plants.

9. The population of plants of claim 8, wherein said refuge plants comprise less than about 10% of said population of plants.

10. A composition for controlling or preventing Cry-resistant *Spodoptera frugiperda* insects, said composition comprising cells that express insecticidally c active amounts of both the Cry1Fa core toxin-containing protein of SEQ ID NO: 4 and the Cry1Ca core toxin-containing protein of SEQ ID NO:5.

11. The composition of claim 10, wherein said cell is a microorganism or a plant cell.

12. The transgenic plant of claim 1, wherein said plant a third protein selected from the group consisting of Vip3A, Cry1D, Cry1Be, and Cry1E proteins.

13. A population of plants comprising non-Bt refuge plants and a plurality of transgenic plants of claim 12, wherein said refuge plants comprise less than about 10% said population to plants.

14. The population of plants of claim 13, wherein said refuge plants comprise less than about 5% of said population of plants.

15. A mixture of seeds comprising refuge seeds from non-Bt refuge plants and a plurality of seeds from the plant of claim 12, wherein said refuge seeds comprise less than 10% of all the seeds in the mixture.

16. The plant of claim 1, wherein said plant is selected from the group consisting of corn, soybeans, and cotton.

17. The plant of claim 16, wherein said plant is a corn plant.

* * * * *